United States Patent [19]

Janssen et al.

[11] 4,060,528
[45] Nov. 29, 1977

[54] AROYL-SUBSTITUTED PHENYLMALONIC ACID DERIVATIVES

[75] Inventors: Paul Adriaan Jan Janssen, Vosselaar (Turnhout); Georges Henri Paul Van Daele, Turnhout; Jozef Martin Boey, Wilrijk (Antwerp), all of Belgium

[73] Assignee: Janssen Pharmaceutica N.V., Beerse, Belgium

[21] Appl. No.: 749,574

[22] Filed: Dec. 10, 1976

Related U.S. Application Data

[60] Division of Ser. No. 620,906, Oct. 8, 1975, Pat. No. 4,035,376, which is a continuation-in-part of Ser. No. 395,877, Sept. 10, 1973, abandoned, which is a continuation-in-part of Ser. No. 300,079, Oct. 24, 1972, abandoned.

[51] Int. Cl.² .............................................. C07D 213/55
[52] U.S. Cl. ......................... 260/295 R; 260/295.5 R; 260/332.2 A; 560/54
[58] Field of Search .................... 260/295 R, 295.5 R, 260/332.2 A, 475 SC

[56] References Cited

U.S. PATENT DOCUMENTS

| | | | |
|---|---|---|---|
| 2,513,572 | 7/1950 | Lee et al. | 260/332.2 A |
| 2,513,573 | 7/1950 | Lee et al. | 260/332.2 A |
| 3,691,202 | 9/1972 | O'Mant | 260/332.2 A |
| 3,824,275 | 7/1974 | Kasubick | 260/475 SC |

*Primary Examiner*—Alan L. Rotman
*Attorney, Agent, or Firm*—Salvatore R. Conte

[57] ABSTRACT

Compounds of the class of aroyl-substituted phenylacetic acids and corresponding esters, amides and hydroxamic acids, useful as anti-inflammatory agents and certain novel precursors therefor.

9 Claims, No Drawings

AROYL-SUBSTITUTED PHENYLMALONIC ACID DERIVATIVES

CROSS-REFERENCE TO RELATED APPLICATIONS

This is a divisional application of our copending application Ser. No. 620,906, filed Oct. 8, 1975, now U.S. Pat No. 4,035,376, which in turn is a continuation-in-part of our application Ser. No. 395,877, filed Sept. 10, 1973, now abandoned, which in turn is a continuation-in-part of application Ser. No. 300,079, filed Oct. 24, 1972, now abandoned.

BACKGROUND OF THE INVENTION

The invention pertains to the field of aroyl-phenylacetic acids, and to esters, amides and hydroxamic acids thereof, which demonstrate anti-inflammatory activity. The subject compounds differ mainly from those of the prior art by the nature of the aroyl function.

The prior art may be represented by the following references:
French Spec. Med. Pat. 8,440M;
French Pat. No. 1,589,691;
French Spec. Med. Pat. 7,956M;
Chem. Abstr., 71, 91097s;
Chem. Abstr., 73, 66268g;
French Pat. No. 1,516,775;
French Spec. Med. Pat. 5,903M;
Chem. Abstr., 73, 77035e; and
French Spec. Med. Pat. 6,444M.

DESCRIPTION OF THE INVENTION

This invention relates to novel aroyl-substituted phenylacetic acids and certain esters, amides and hydroxamic acids thereof. Said novel compounds may be represented by the following formula:

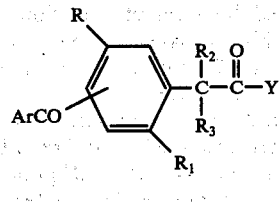

(I)

wherein:
ArCO is an aroyl substituent the Ar function of which is a member selected from the group consisting of 2-thienyl, 5-loweralkyl-2-thienyl, preferably 5-methyl-2-thienyl, 5-halo-2-thienyl, preferably 5-chloro-2-thienyl, 2-naphthyl and 3-pyridyl, said ArCO being in the meta- or para-position relative to the acetic acid function;

either of R and $R_1$ is hydrogen, the other being a member selected from the group consisting of hydrogen, halo, preferably chloro, and loweralkyl, preferably methyl, provided that, when said R is halo or loweralkyl, then said ArCO is in the aforementioned para-position, and when said $R_1$ is halo or loweralkyl, then said ArCO is in the aforementioned meta-position, and further provided that when said R or $R_1$ is halo, then said Ar is a member selected from the group consisting of 2-thienyl, 5-loweralkyl-2-thienyl and 5-halo-2-thienyl;

either of $R_2$ and $R_3$ is a member selected from the group consisting of hydrogen, allyl and loweralkyl, the other being a member selected from the group consisting of hydrogen and loweralkyl, provided that, when either of said $R_2$ and $R_3$ is allyl, the other is hydrogen, and when either of said $R_2$ and $R_3$ is loweralkyl, the other is a member selected from the group consisting of hydrogen and loweralkyl;

$R_2$ and $R_3$, when taken together, is an alkylene bridge attached to the α-carbon of the acetic acid function:

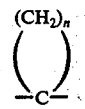

wherein
n is an integer from 2 to 5; and
Y is a member selected from the group consisting of hydroxy, alkoxy having from 1 to 8 carbon atoms, diloweralkylaminoloweralkyloxy and aminoradicals of the class consisting of —$NH_2$, anilino, halo-substituted anilino, preferably chloroanilino, loweralkyl-anilino, such as methylanilino, loweralkyloxy-anilino, preferably methoxyanilino, piperidino, —NH—$CH_2$—$CH_2OH$, 2-(2-thiazolinyl)amino, —NHOH; when Y stands for the radical —NHOH, the tautomeric hydroxamic acid form is intended to be within the scope of the invention.

As used herein, "loweralkyl" may be straight or branch chained and have from 1 to 5 carbon atoms, such as for example, methyl, ethyl, propyl, isopropyl, butyl, pentyl and the like. The term "halo" is generic to fluoro, chloro, bromo and iodo.

A preferred subgenus of the instant invention relates to those aroyl substituted α-$R_2$-α-$R_3$-phenylacetic acid derivatives of the formula (I) embraced by the formula:

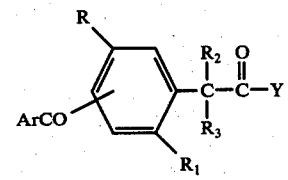

wherein:
ArCO is an aroyl substituent the Ar function of which is a member selected from the group consisting of 2-thienyl, 5-loweralkyl-2-thienyl and 5-halo-2-thienyl, said ArCO being in the meta- or para-position relative to the acetic acid function;

either of R and $R_1$ is hydrogen, the other being a member selected from the group consisting of hydrogen, halo and loweralkyl, provided that, when said R is halo or loweralkyl, then said ArCO is in the aforementioned para-position, and when said $R_1$ is halo or loweralkyl, then said ArCO is in the aforementioned meta-position;

either of $R_2$ and $R_3$ is a member selected from the group consisting of hydrogen, allyl and loweralkyl the other being a member selected from the group consisting of hydrogen and loweralkyl, provided that, when either of said $R_2$ and $R_3$ is allyl, the other is hydrogen, and when either of said $R_2$ and $R_3$ is loweralkyl, the other is a member selected from the group consisting of hydrogen and loweralkyl;

$R_2$ and $R_3$, when taken together, is an alkylene bridge attached to the α-carbon of the acetic acid function:

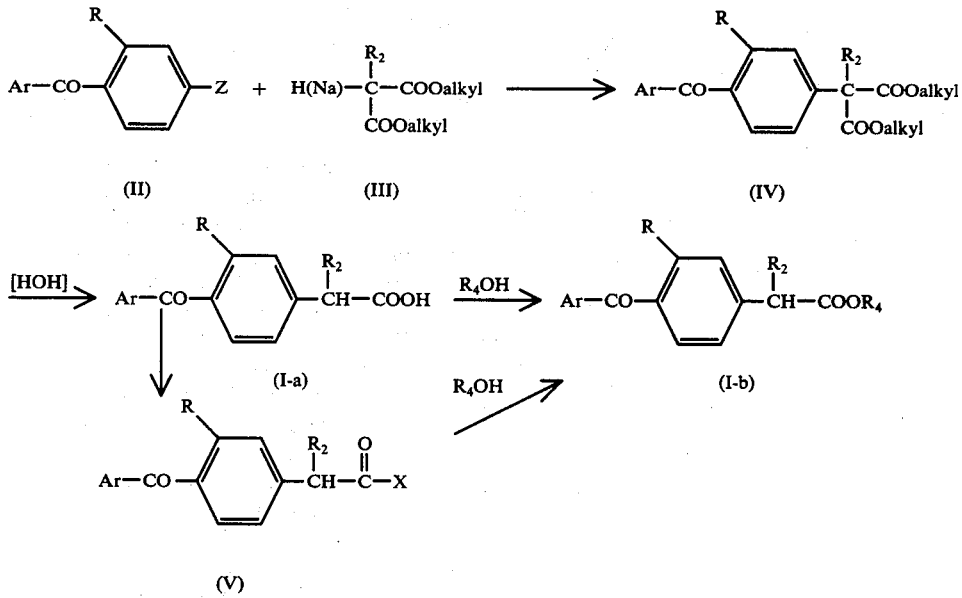

wherein n is an integer from 2 to 5; and

Y is a member selected from the group consisting of hydroxy, alkoxy having from 1 to 8 carbon atoms and diloweralkylamino-loweralkoxy.

The para-aroyl-substituted phenylacetic acid derivatives of formula (I), wherein $R_3$ is hydrogen, are conveniently prepared by reacting an appropriate aryl-ketone of formula (II) wherein Ar and R are as previously defined, and Z is an appropriate leaving group, preferably a fluorophenyl-arylketone, with an appropriate diloweralkyl-2-$R_2$-malonate of formula (III), preferably the diethyl ester, in a suitable reaction-inert organic solvent. It is advantageous to displace the active hydrogen in the 2-position of (III) with alkali metal, preferably sodium, by treatment with an appropriate base, for example, an alkali metal hydride such as sodium hydride, prior to reaction with (II). As employed herein, the term "reaction-inert organic solvent" is meant to include any organic liquid which will solubilize or disperse the reactants (II) and (III) and not interfere with their interaction, for example, hexamethylphosphoramide, nitromethane, dimethylsulfoxide, dimethylformamide and the like. The thus-obtained di-ester (IV) is then hydrolyzed, preferably utilizing alkaline hydrolysis conditions, for example, by heating a mixture of (IV) with alkali metal hydroxide solution to form the corresponding alkali metal salt of the corresponding acid and then acidifying the resultant salt to yield the desired phenylacetic acids (I-a). The latter may then be subjected to standard esterification procedures, for example, (a) by treatment with an appropriate alcohol ($R_4$OH) in acid medium, or (b) by first converting the acid to the corresponding alkali metal salt form by treatment with an appropriate alkali metal base, e.g., sodium hydride, and then reacting said salt with an appropriate $R_4$-halide in an appropriate polar solvent; or (c) by converting the acid to the acid-halide and then reacting said acid-halide with the appropriate alcohol to yield the desired esters (I-b) wherein Ar, R and $R_2$ are as previously defined and $R_4$ is alkyl or diloweralkylaminoloweralkyl. The foregoing reactions may be illustrated by the following schematic diagram:

Moreover, esters of formula (I-b) may also conveniently be prepared by transesterification of a loweralkylester with a higher alkanol or with the appropriate dialkylaminoalkanol for example in the presence of an alcaline reaction promotor.

It has been found that the aforementioned reaction between (II) and (III) can yield a mixture of the di-ester (IV) and the mono-ester (IV-a), said mono-ester proceeding from decomposition of the di-ester:

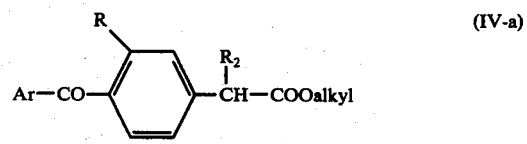

The mono-ester, which can be isolated by conventional means, for example, by distillation, is then subjected to standard ester-to-acid hydrolysis to yield the desired phenylacetic acid derivative of formula (I-a).

The diloweralkyl malonates of formula (IV) are deemed to be novel compounds and, in view of their utility as precursors for making the compounds of formula (I), they constitute an additional feature of this invention.

Aryl ketones of formula (II) are readily obtained by a Friedel-Crafts reaction between an appropriate aromatic compound of the formula: Ar-H, wherein Ar is thienyl, 5-halo-2-thienyl or 5-loweralkyl-2-thienyl, and an appropriate carbonyl halide, preferably the chloride, of the formula:

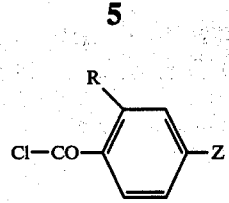

wherein R and Z are as previously defined, in the presence of a Lewis acid, preferably a metallic halide such as aluminum chloride, stannic chloride and the like in a suitable solvent such as is typically employed in a Friedel-Crafts type of reaction, for example, methylene chloride, 1,2-dichloroethane, carbon disulfide, nitrobenzene, anhydrous benzene (with $SnCl_4$) and the like. Conversely, the formula (II) ketones may be obtained by a Friedel-Crafts reaction between an appropriate substituted benzene of the formula

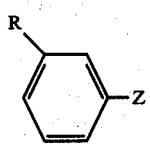

wherein R is hydrogen or loweralkyl and Z is as previously defined, preferably fluoro, and an appropriate aryl carbonyl halide, preferably the chloride, of the formula: Ar—CO—Cl, wherein Ar is as previously defined.

Several of the fluorophenyl aryl ketones of formula (II-a) are also deemed to be novel and, n view of their utility as precursors herein, such ketones constitute a further aspect of this invention. These novel ketones may be represented by the following generic formula:

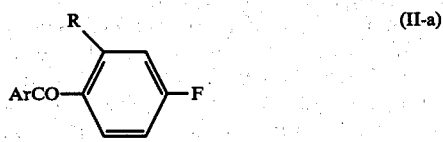

wherein ArCO is an aryl carbonyl substituent the Ar function of which is a member selected from the group consisting of 2-thienyl, 5-chloro-2-thienyl, 5-methyl-2-thienyl, and 3-pyridyl; R is a member selected from the group consisting of hydrogen, halo and loweralkyl; provided that, when said Ar is 2-thienyl, then said R is halo or loweralkyl, and provided that when said R is halo, then said Ar is 2-thienyl, 5-2-thienyl or 5-loweralkyl-2-thienyl.

The compounds of formula (I) wherein Y stands for an aminoradical are easily obtained by known methods for the preparation of amides or hydroxamic acids. For example, they are obtained by treating a loweralkylester of formula (I-b) with an appropriate amine or acid addition salt thereof in alkaline medium, or by reacting an acylhalide of formula (V) with an appropriate amine in a suitable solvent.

Meta- and para-aroylphenylacetic acids of formula (I) wherein Y is OH; and ArCO, R, $R_1$, $R_2$ and $R_3$ are as previously defined, may be prepared by conventional nitrile-to-acid hydrolysis of the corresponding aroyl phenylacetonitriles of formula (VI), for example by refluxing the nitrile with a strong acid such as for example aqueous sulfuric acid (20 - 70%); with concentrated sulfuric acid in the presence of glacial acetic acid; or with alkaline hydrolysis such as potassium hydroxide in an alcohol.

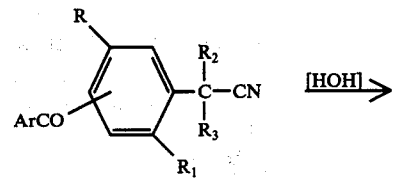

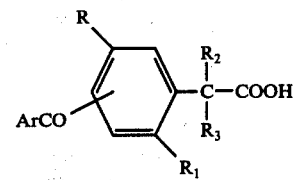

The resulting phenylacetic acids of formula (I-c) are easily converted into the corresponding compounds of formula (I) as previously defined, by conventional methods.

Phenylacetonitriles of formula (VI-a), wherein ArCO and $R_2$ are as previously defined, R and $R_1$ are hydrogen or loweralkyl, may be prepared by the following reaction sequence: an approximately equimolar mixture of m- or p-bromobenzyl alcohol (VII) and 3,4-dihydropyran (VIII), to which HCl has been added, is allowed to react in the cold (about $-10°$ to $0°$ C). The thus-obtained 2-(bromobenzyloxy)tetrahydropyran (IX), which can be isolated by conventional techniques, is then converted into a Grignard complex by standard treatment with magnesium in a suitable solvent, such as, for example, tetrahydrofuran, and said Grignard complex is reacted with an appropriate aryl nitrile of formula (X), wherein Ar is as previously defined, to yield the resultant ketone of formula (XI). The hydroxy function of the latter ketone is transformed into a reactive ester function (XII) by treatment with an appropriate agent, preferably a chlorinating or brominating agent, such as thionyl chloride, phosphorous tribromide and the like, in a suitable solvent, for example, aromatic hydrocarbons, such as benzene, toluene, xylene and the like, ethers, such as diethyl ether, dioxane and the like, and halohydrocarbons, such as chloroform and the like. In turn, the reactive ester function is transformed into a nitrile function (VI-a), for example by treating (XII) with sodium cyanide in a suitable solvent, such as dimethyl sulfoxide. Slightly elevated temperatures (50°–60° C) may be employed to enhance the rate of reaction.

The foregoing reaction sequence is illustrated by the following schematic diagram:

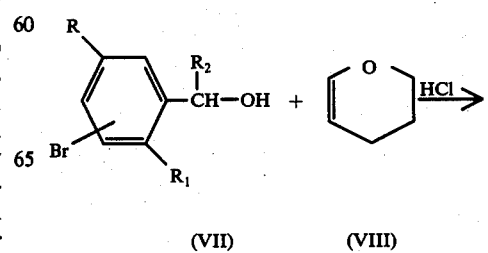

-continued

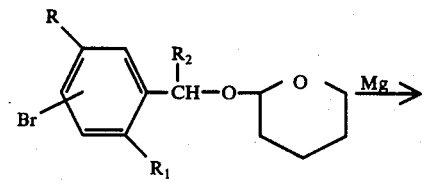

(IX)

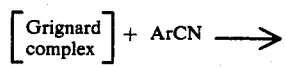

(X)

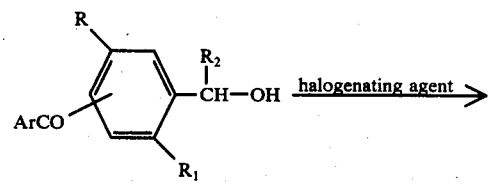

(XI)

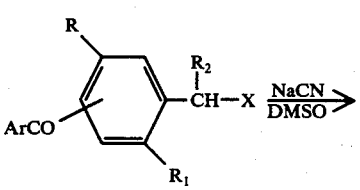

(XII)

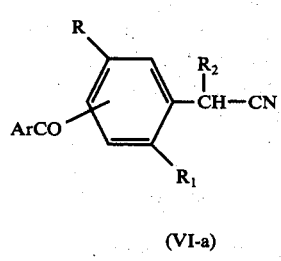

(VI-a)

Compounds of formula (VI-c) wherein Ar is thienyl, 5-halo-2-thienyl, 5-loweralkyl-2-thienyl, 3-pyridyl and 2-naphthyl; R and $R_1$ are hydrogen, halo, preferably chloro, or loweralkyl, may be prepared by monoalkylation of an α-unsubstituted phenylacetonitrile of formula (VI-b). This may be achieved by reacting (VI-b) in an alkaline aqueous medium, for example, in a 50%-aqueous sodium hydroxide solution with an equivalent amount of a suitable alkylhalide in the presence of a quaternary ammonium salt, preferably N-benzyl-triethylammonium chloride.

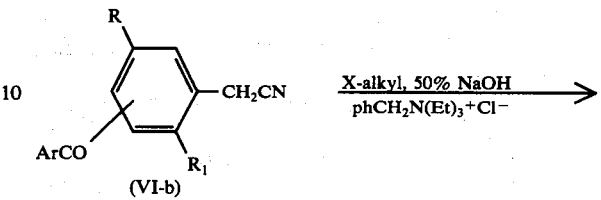

(VI-b)

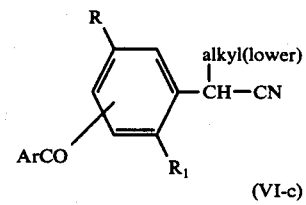

(VI-c)

Monoalkylation of (VI-b) may also be carried out by reacting (VI-b) with an alkylhalide, in liquid ammonia, in the presence of an equivalent amount of sodiumamide.

Monoalkylation is also achieved by reacting (VI-b) with an alkylhalide in the presence of a suitable metallating agent, such as sodium hydride in a suitable polar solvent, provided that the alkyl group sterically prevents dialkylation, as is the case for example with a branched alkyl group, such as isopropyl, isobutyl and the like.

α-Diloweralkyl aroyl phenylacetonitriles of formula (VI-d), are conveniently prepared by di-alkylation of (VI-b). Di-alkylation may be carried out by reacting a phenylacetonitrile of formula (VI-b) with an appropriate alkylhalide, preferably an alkyliodide, in a suitable organic solvent, such as for example, hexamethylphosphoramide, nitromethane, dimethylformamide, dimethylsulfoxide and the like, in the presence of an appropriate base, preferably a metal hydride, such as sodium hydride. When the alkylation is carried out with an appropriate amount of an appropriate alkylene dihalide, a cyclic homolog of formula (VI-e) is obtained, wherein $(CH_2)_n$ is an alkylene chain having from 2 to 5 carbon atoms.

Alternatively when an α-alkyl aroylphenylacetonitrile is alkylated under similar conditions, an α-dialkyl aroyl phenylacetonitrile (VI-f) is obtained wherein $R_3$ may be a different loweralkyl radical.

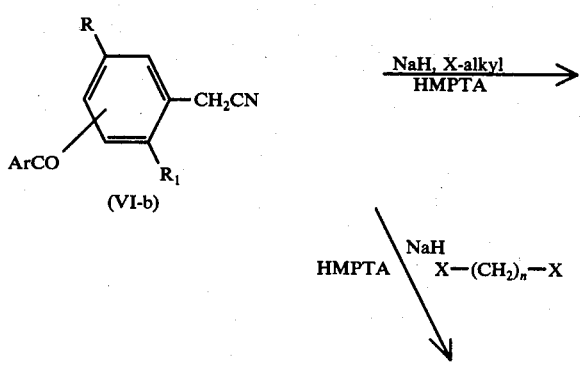

(VI-b)

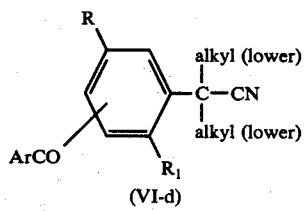

(VI-d)

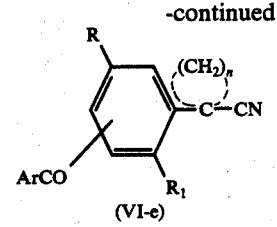
(VI-e)

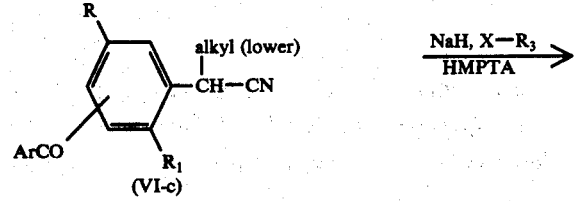
(VI-c)     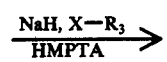     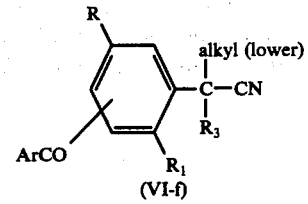
(VI-f)

Aroylbenzylhalides of formula (XII-a) wherein Ar is 2-thienyl, 5-halo-2-thienyl, 5-loweralkyl-2-thienyl or 2-naphthyl; R and $R_1$ are hydrogen or halo and $R_2$ is hydrogen or loweralkyl, may be prepared by brominating a suitable meta- or para-alkylphenyl aryl ketone of formula (XIII) with a convenient brominating agent, such as N-bromosuccinimide in an appropriate reaction-inert organic solvent, such as for example, carbon-tetrachloride in the presence of a peroxide, such as benzoyl peroxide. The reaction is preferably carried out at elevated temperatures.

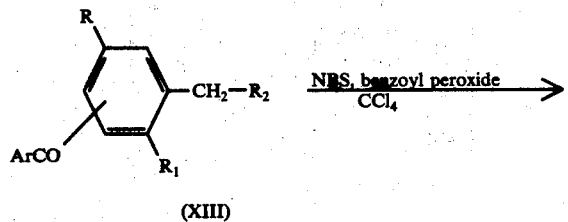
(XIII)

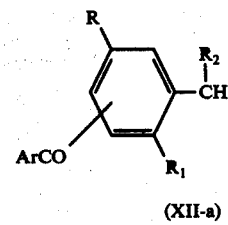
(XII-a)

It is understood that the bromides of formula (XII-a) may easily be converted to the corresponding nitriles by conventional means.

Said alkylphenyl aryl ketones of formula (XIII) may be prepared for example by reacting a meta- or para-alkyl benzoyl halide (XIV) with an ArH compound under Friedel-Crafts conditions:

ArH + 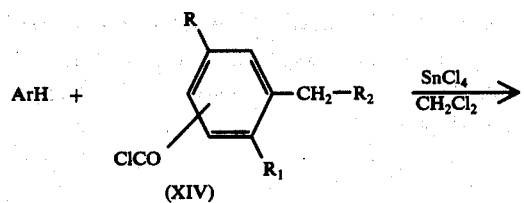
(XIV)

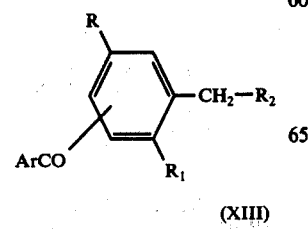
(XIII)

The compounds of formula (XII-b), wherein $R_2$ is as previously defined, Ar is 2-thienyl, 5-halo-2-thienyl or 5-loweralkyl-2-thienyl and X is halo, may be prepared by reacting a α-haloalkyl benzoyl halide of formula (XV) with an ArH compound in mild Friedel-Crafts conditions whereby acylation of the aryl compound selectively occurs.

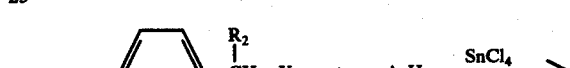
(XV)

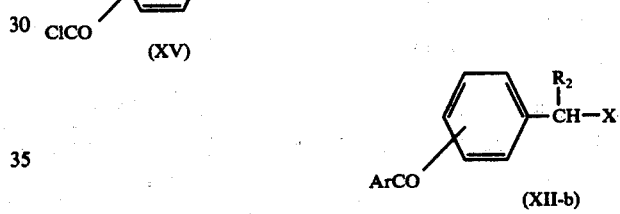
(XII-b)

Another method for the preparation of the meta- and para-aroyl benzylalcohols of formula (XI-a), wherein Ar, R and $R_1$ are previously defined and $R_2$ is hydrogen or loweralkyl consists in a selective reduction of a ketone of formula (XVI) with an equivalent amount of a suitable hydrogenating agent, such as a metal borohydride, preferably sodium borohydride or sodium cyanoborohydride in a suitable organic solvent, for example a lower alkanol, such as methanol, ethanol, is isopropanol and the like, or with lithium aluminum hydride - tert. butoxide preferably in an ether, such as for example diethyl ether, tetrahydrofuran, dioxane and the like.

(XVI)

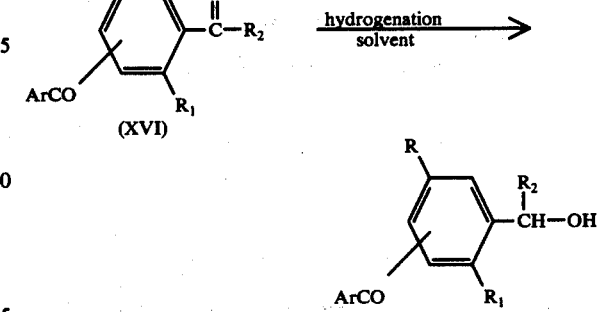
(XI-a)

Compounds of formula (XVI) wherein Ar is as previously defined and R, $R_1$ and $R_2$ are hydrogen or loweralkyl, may be prepared starting from m- or p-bromobenzoyl derivatives of formula (XVII), the carbonyl function of which is previously protected by a suitable protecting group for example by ketalization. The resulting cyclic acetal or ketal of formula (XVIII) is then converted into a Grignard complex by standard treatment with magnesium in a suitable solvent and said Grignard complex is reacted with an appropriate arylnitrile.

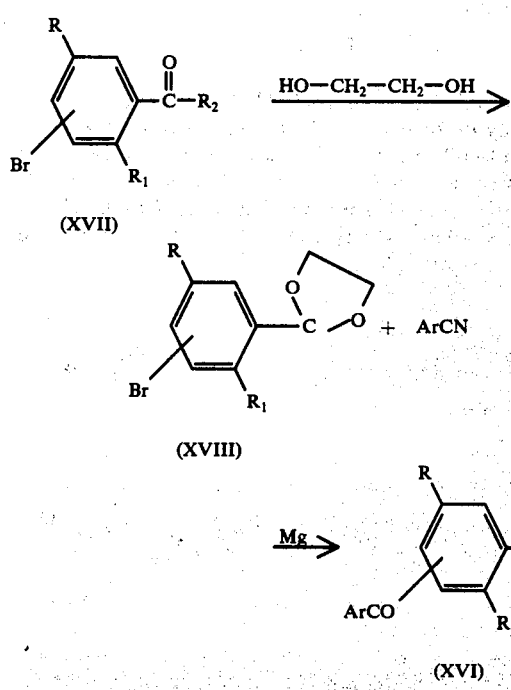

The compounds of formula (VI), (XI), (XII) and (XVI) are deemed to be novel and as useful precursors for the preparation of compounds of formula (I) they constitute an additional feature of this invention.

The α-unsubstituted aroyl phenylacetic acids of formula (I-d) may also be prepared from acetophenones of formula (XVI-a) by application of the Willgerodt reaction.

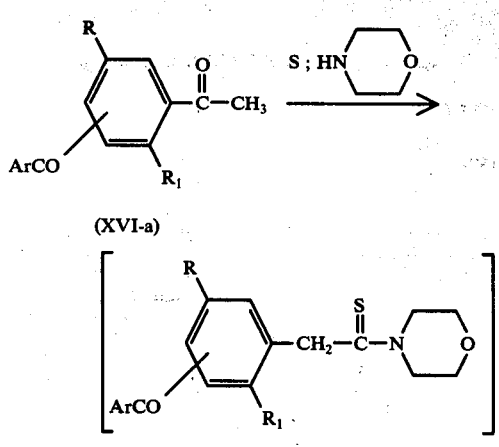

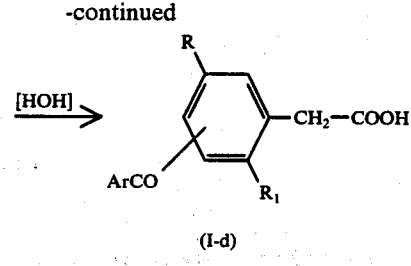

Aroylhydratropic acids of formula (I-e) are conveniently prepared by a modified Willgerodt reaction as illustrated by the following scheme:

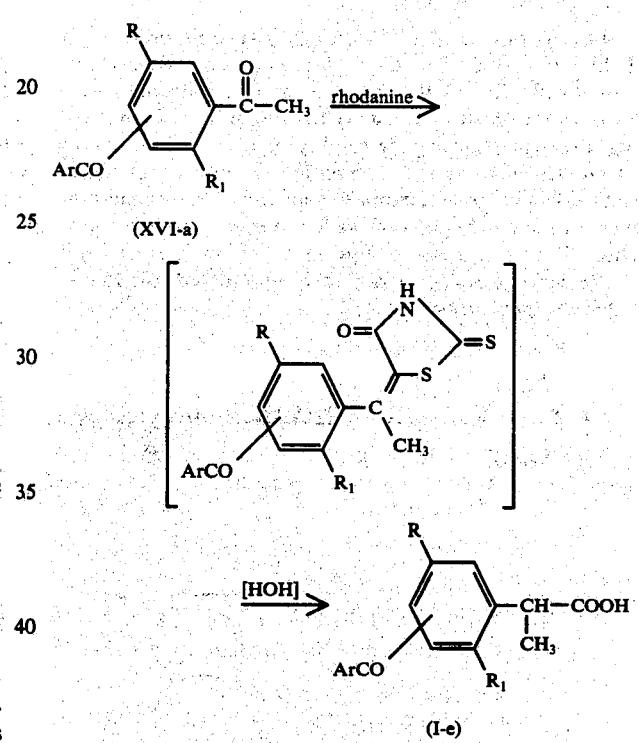

An alternative method for the preparation of α-loweralkyl aroyl phenylacetic acids of formula (I-f) consists in the alkylation of the corresponding α-unsubstituted aroyl phenylacetic acids (I-d). One of the activated α-hydrogen atoms is first metallated, for example by treatment of the acid with an appropriate metallating agent such as sodium amide in liquid ammonia. An alkylhalide, preferably an alkyliodide is then added and the resulting α-alkyl aroyl phenylacetic is purified by conventional means.

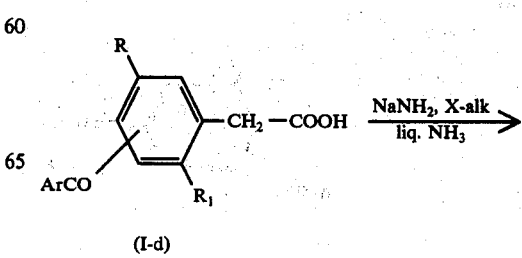

-continued

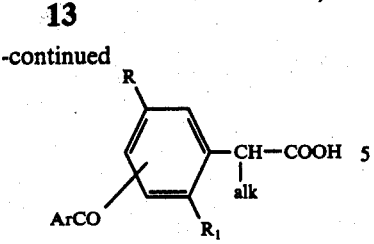

(I-f)

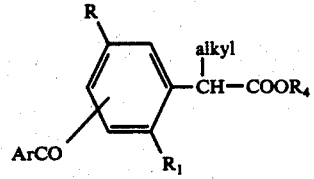

(I-h)

Esters of aroyl phenylacetic acids (I-g), wherein Ar, R, $R_1$ and $R_4$ are as previously defined, may also be mono- or di-alkylated in the α-position. In one method the ester is first treated with an appropriate amount of a metallating agent such as for example sodiumhydride in a suitable reaction-inert organic solvent such as for example, dimethylformamide, dimethylsulfoxide, hexamethylphosphoramide and the like and then reacted with an appropriate amount of an appropriate alkylhalide to form the α-alkyl substituted compounds.

The resulting esters are readily converted into the corresponding acids and the corresponding derivatives thereof of general formula (I), by conventional methods.

An alternative method for the preparation of p-aroyl hydratropic acids wherein Ar is as herebefore defined; R, $R_1$ and $R_3$ are hydrogen and $R_2$ is methyl is given in the following reaction sequence. A p-formylhydratropic acid alkylester of formula (XIX) is converted into the corresponding di-carboxylic acid monoester of for-

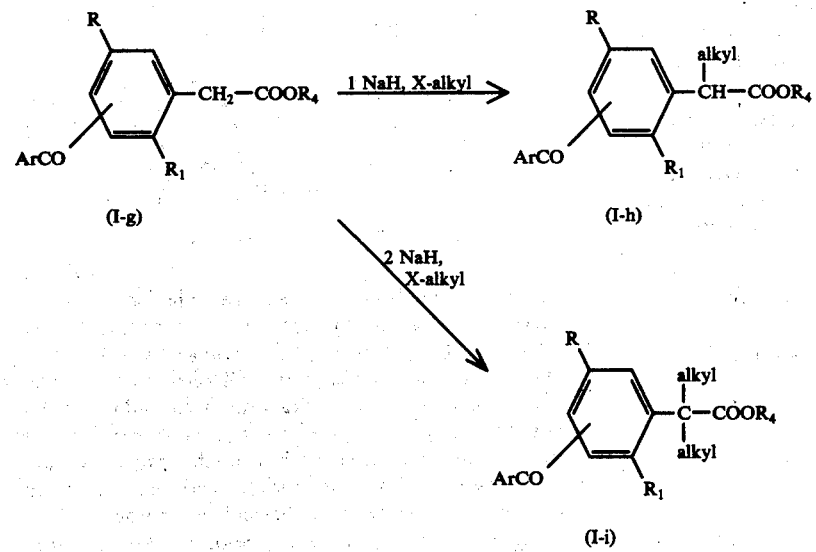

Another method comprises the transformation of an ester of formula (I-g) into a metal enolate, preferably the lithium enolate by treating the ester with a suitable lithium amide, preferably the lithium-diisopropylamide in tetrahydrofuran and then reacting it with a convenient alkylating agent such as an alkylhalide, preferably in the presence of hexamethylphosphoramide.

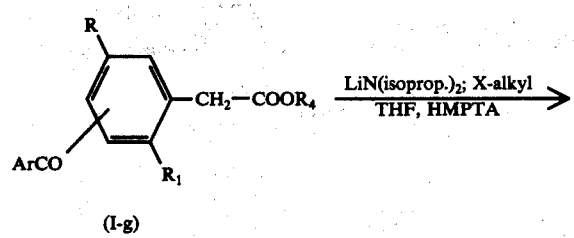

mula (XX) by oxidation, preferably under neutral conditions such as for example with hydrogen peroxide in acetone, with silveroxide in water or dioxane or with oxygen in the presence of finely divided silver in a suitable reaction-inert organic solvent, such as dioxane, benzene, toluene, xylene and the like. The carboxyl group is then selectively converted into an halocarbonyl group by known methods such as for example, by treatment with thionyl chloride in chloroform in the presence of a trace of pyridine as reaction promotor.

The resulting acylhalide is then reacted with an aromatic compound under Friedel-Crafts conditions, yielding the acid of formula (I-j).

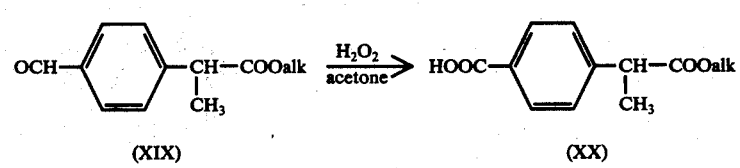

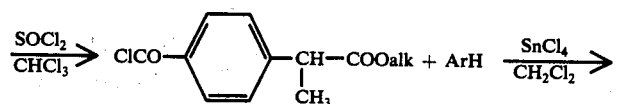

(XXI)

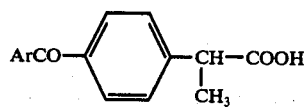

(I-j)

Still another method for the preparation of aroyl phenylacetic acids of formula (I-f) is given in the following reaction sequence. An α-unsubstituted phenylacetonitrile of formula (VI-b) is first carbalcoxylated or a loweralkyl chloroformate in the presence of an alcaline condensing agent such as for example sodium amide or sodium ethoxide. The resulting compound of formula (XXII) is then alkylated by conventional methods such as for example with an alkylhalide in the presence of an appropriate alcaline condensing agent such as sodium or potassium ethoxide. The resulting cyanacetic acid derivative of formula (XXIII) is then hydrolysed and decarboxylated by known methods, such as for example by heating (XXIII) with alkali in an appropriate organic solvent such as ethanol, yielding the desired compound of formula (I-f). The foregoing is illustrated by the following reaction scheme:

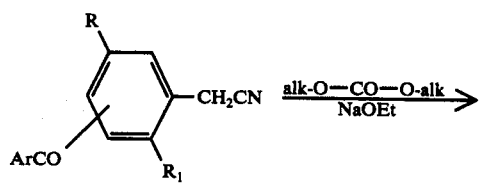

(VI-b)

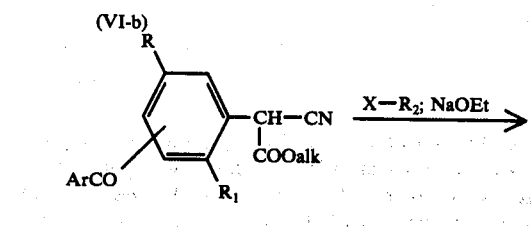

(XXII)

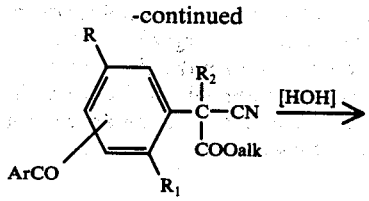

(XXIII)

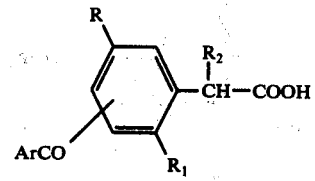

(I-f)

Alternative methods are also available for the transformation of aroylbenzoyl derivatives of formula (XVI-b) into phenylacetonitriles of formula (VI-c). One such method comprises the reaction of (XVI-b) with tosylhydrazine whereby a tosylhydrazone of formula (XXIV) is formed. The resulting tosylhydrazone is then reacted with hydrocyanic acid or with a suitable metal cyanide in the presence of an appropriate acid such as acetic acid in an appropriate solvent such as methanol. The decomposition of (XXV), yielding the desired phenylacetonitrile, may be carried out by decomposition with alkali or by heating (XXV) in a bath of decalin. The foregoing reaction sequence is illustrated in the following reaction scheme:

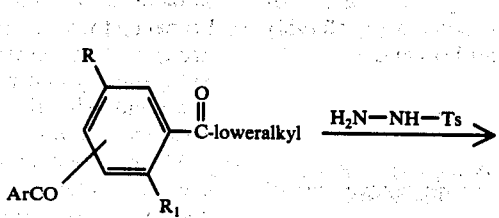

(XVI-b)

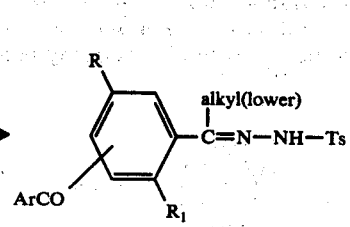

(XXIV)

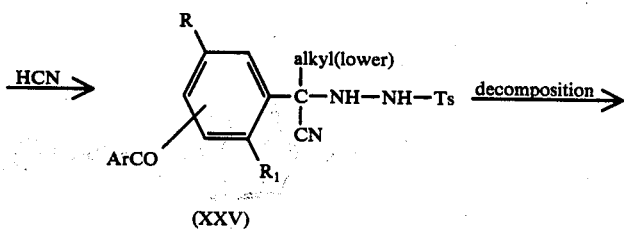

(XXV)

-continued

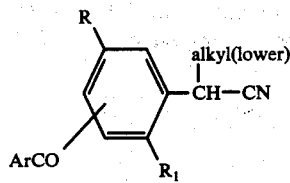

(VI-c)

A further method consists in treating (XVI-b) with methyl carbazate and the resulting methoxycarbonylhydrazone is reacted with hydrocyanic acid yielding the corresponding hydrazide of formula (XXVII). The hydrazide is then oxidized for example with bromine, and the resulting diazene of formula (XXVIII) is decomposed for example using sodium methoxide in methanol whereby the desired phenylacetonitrile is obtained:

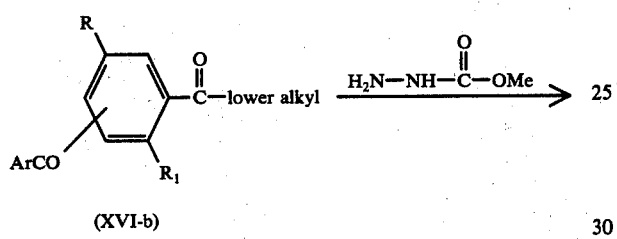

(XVI-b)

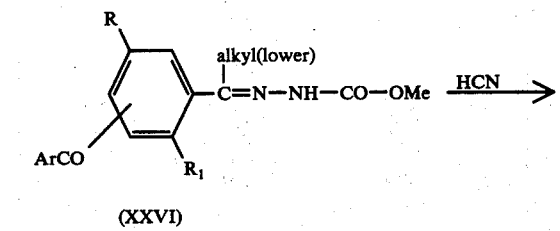

(XXVI)

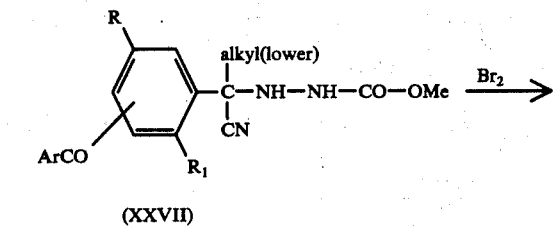

(XXVII)

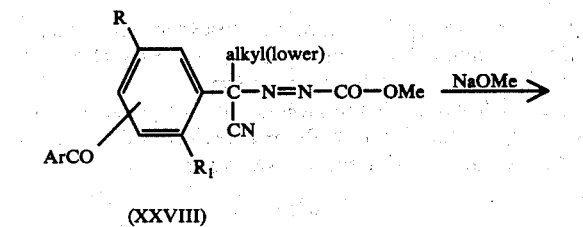

(XXVIII)

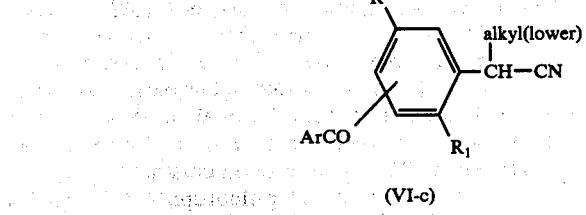

(VI-c)

In another method a compound of formula (XVI-b) is reacted with tosylmethylisocyanide in the presence of an appropriate amount of sodium ethoxide in a suitable solvent such as dimethoxyethane, yielding the desired compounds of formula (VI-c):

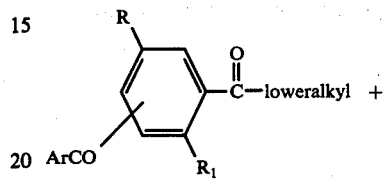

(XVI-b)

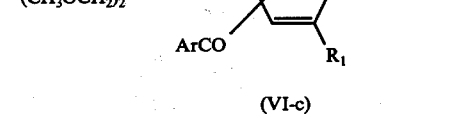

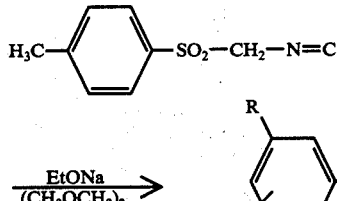

(VI-c)

Due to the available asymmetric $\alpha$-carbon atom present in the subject compounds (I), it is evident that their existence in the form of stereochemical isomers (enantiomorphs) is possible. By standard methods of resolution the corresponding (−) or (+) forms of the desired compounds are obtainable. Such pharmacologically active enatiomorphs are naturally intended to be included within the scope of this invention.

The subject compounds (I) possess useful anti-inflammatory properties as demonstrated by their activity in the HOAc-induced writhing test and/or in the mycobacterium butyricum test. In these tests, the subject compounds have been found to be potent antagonists of acetic acid induced writhing in rats and/or of mycobacterium butyricum induced arthritis in rats.

According to the acetic acid induced writhing test, female Wistar rats (body weight 100±5g) are fasted overnight and injected intraperitoneally with 0.5 ml of a 1% acetic acid solution. Rats with at least 10 writhes within the first 10 minutes following the acetic acid injection are selected and treated 5 minutes later with an oral dose of the compound under investigation or with the vehicle (control). The number of writhes, i.e. the backward extension of the hind limbs, are counted during a 15 minute experimental session 45 to 60 minutes after the oral treatment. A minimum of three rats are used for each dose level tested. A significant drug effect is said to occur if the number of writhes counted during the experimental session of 15 minutes is less than 15 since this is significantly ($P < 0.05$) different from controls.

The data given below show the lowest effective oral dose expressed as $ED_{50}$ (mg/kg), of the preferred compound A, p-(2-thenoyl)-α-methyl-phenylacetic acid, compared with the corresponding phenyl compound B, p-benzoyl-α-methylphenylacetic acid, calculated on the all-or-none basis of less than 15 writhes per animal per session. Under these experimental conditions, the former compound is shown to be 16 times more active than the latter compound.

| Compound | Oral ED$_{50}$ (mg/kg) | Potency Ratio |
|---|---|---|
| A | 0.08 | ① |
| B | 1.25 | 1/16 |

According to the mycobacterium butyricum induced arthritis test, male Wistar rats (body weight 235±15g) are injected intradermally in the tail base with 0.05 ml of an oily suspension of mycobacterium butyricum. The paws and the joint diameters of the hind limbs are measured the day of the injection and a fortnight later. Rats with established arthritis, i.e., significant increase in paw and joint diameters are used for drug testing. Groups of three individually caged animals receive the drug under investigation mixed with the powdered food at different concentrations during 14 consecutive days. After this treatment period, the diameters of the hind limbs are measured again and the effect of drug treatment is evaluated by comparing the final swelling degrees of treated animals with that occurring in untreated controls. The lowest effective dose is that dose whereby a significant decrease of the swelling is observed as compared to untreated control animals.

The data given below shown the lowest effective dose of the preferred compound A again compared with the corresponding phenyl compound B. Under these experimental conditions the former compound is shown to be a powerful antagonist of mycobacterium butyricum induced arthritis in rats, being at least 16 times more active than the latter compound.

| Compound | Lowest Effective Dose | Potency Ratio |
|---|---|---|
| A | 0.63 | ① |
| B | 10.0 | 1/16 |

In the following table, data with respect to other compounds embraced by formula (I) are given, it being understood that such compounds are not listed for purposes of limiting the invention thereto, but only to exemplify the useful anti-inflammatory properties of all the compounds within the scope of formula (I).

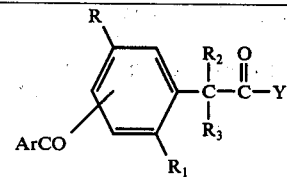

| ArCO | R | R$_1$ | R$_2$ | R$_3$ | Y | Writhing test in rats; ED$_{50}$ in mg/kg | Mycobacterium butyricum test effective dose in mg/kg |
|---|---|---|---|---|---|---|---|
| p-(2-thenoyl) | Cl | H | Me | H | OH | 1.25 | 1.25 |
| p-(3-pyridylcarbonyl) | H | H | Me | H | OH | 2.5 | 2.5 |
| p-(5-Me-2-thenoyl) | H | H | Me | H | OH | 1.25 | 5.0 |
| p-(2-naphtoyl) | H | H | Me | H | OH | 1.25 | 10. |
| m-(2-thenoyl) | H | H | Me | H | OH | 1.25 | — |
| p-(2-thenoyl) | H | H | Me | H | OEt | 0.31 | — |
| p-(2-thenoyl) | H | H | Me | H | OOct | 0.63 | — |
| p-(2-thenoyl) | H | H | Et | H | OH | 0.63 | — |
| p-(2-thenoyl) | H | H | allyl | H | OH | 1.25 | 10. |
| p-(2-thenoyl) (+) | H | H | Me | H | OH | 0.31 | ≦2.5 |
| p-(2-thenoyl) (−) | H | H | Me | H | OH | 5.0 | — |
| p-(2-thenoyl) | H | H | Me | H | O—(CH$_2$)$_3$—N(Me)$_2$ | 0.16 | 2.5 |
| p-(2-thenoyl) | H | H | Me | H | O—(CH$_2$)$_2$—N(Et)$_2$ | 0.04 | 2.5 |
| p-(2-thenoyl) | Me | H | Me | H | OH | 5.0 | 10. |
| p-(2-thenoyl) | H | H | Me | Me | OH | 0.31 | <10. |
| p-(2-thenoyl) | H | H | Me | H | O—(CH$_2$)$_2$—N(Me)$_2$ | 0.08 | 2.5 |
| p-(5-chloro-2-thenoyl) | H | H | Me | H | OH | 0.63 | 5.0 |
| p-(2-thenoyl) | H | H | Me | H | NHOH | 1.25 | — |
| m-(2-thenoyl) | H | Me | H | H | OH | 10. | 1.25 |
| p-(2-thenoyl) | H | H | Me | H | NH—⟨C$_6$H$_4$⟩—OCH$_3$ | 10. | <10 |
| p-(2-thenoyl) | H | H | Me | H | NH—(thiazoline) | 2.5 | 10 |

As was already demonstrated with other anti-inflammatory agents, the compounds of formula (I) were found to inhibit platelet aggregation.

The following examples are intended to illustrate, but not to limit, the scope of the present invention. Unless otherwise stated, all parts are by weight.

EXAMPLE I 9.6 parts of sodium hydride dispersion 55% are suspended three times in anhydrous benzene and the latter is each time decanted. Then there are added successively 200 parts of hexamethylphosphoramide and dropwise 34.8 parts of diethyl 2-methylmalonate. The mixture is warmed gently, whereupon a vigorous reaction takes place. When the reaction ceases, the mixture is cooled and 41.2 parts of p-fluorophenyl 2-thienyl ketone are added. The whole is heated to 100° C and stirred at this temperature for 10 hours. The reaction mixture is diluted with 400 parts of benzene, washed twice with water, dried and evaporated. The oily residue is distilled, yielding diethyl 2-methyl-2-[p-(2-thenoyl)phenyl]malonate; bp. 205°–210° C at 0.4 mm. pressure.

A mixture of 30.3 parts of diethyl 2-methyl-2-[p-(2-thenoyl)phenyl]malonate and 200 parts of sodium hydroxide solution 5% is stirred and refluxed for 6 hours. The reaction mixture is allowed to cool while stirring. The whole is filtered and the aqueous phase is separated. The latter is washed with benzene, acidified with concentrated hydrochloric acid solution and stirred for 15 minutes. The product is extracted with chloroform. The extract is washed with water, dried, filtered and evaporated. The oily residue is triturated twice in petroleumether. The solid product is filtered off and crystallized twice from acetonitrile: first at −20° C and then at 0° C, yielding p-(2-thenoyl)hydratropic acid; mp. 124.3° C; also named p-(2-thenoyl)-α-methyl-phenylacetic acid.

EXAMPLE II

A mixture of 5.2 parts of p-(2-thenoyl)hydratropic acid. 40 parts of absolute denatured ethanol and 0.5 parts of hydrochloric acid solution is stirred and refluxed for 24 hours. The reaction mixture is evaporated and the residue is taken up in ether. The ethereal solution is shaken with alkaline water, separated and shaken twice with water. The ether phase is dried, filtered and evaporated, yielding ethyl p-(2-thenoyl)hydratropate, also named ethyl p-(2-thenoyl)-α-methyl-phenylacetate, as a residue.

EXAMPLE III

To a stirred mixture of 5.2 parts of p-(2-thenoyl)hydratropic acid in 50 parts of dry hexamethylphosphoramide are added 0.86 parts of sodium hydride dispersion 55.3% and the whole is stirred for 1.5 hours. Then there are added 3.86 parts of octyl bromide and 0.01 parts of potassium iodide. Upon completion, stirring is continued for 18 hours at room temperature. The reaction mixture is poured onto benzene and the whole is shaken successively twice with water, twice with sodium hydroxide solution and again twice with water. The organic phase is dried, filtered and evaporated. The residue is taken up in ether and stirred with activated charcoal. The latter is filtered off and the filtrate is evaporated again. The residue is purified by column-chromatography with chloroform. The pure fractions are collected and the solvent is evaporated, yielding octyl p-(2-thenoyl)-hydratropate as a residue.

EXAMPLE IV

To a stirred mixture of 25.25 parts of thiophene, 58.1 parts of 2-chloro-4-fluorobenzoyl chloride and 200 parts of anhydrous benzene are added dropwise 78.16 parts of stannic chloride (fuming) at room temperature (slightly exothermic reaction: the temperature is kept for 3 hours at 25° C). The reaction mixture is poured onto a mixture of crushed ice and concentrated hydrochloric acid solution. The whole is stirred for a few minutes and the layers are separated. The organic layer is diluted with 80 parts of toluene, washed successively with 200 parts of sodium hydroxide solution 5% and with 200 parts of water, dried and evaporated. The residue is distilled, yielding 2-chloro-4-fluorophenyl 2-thienyl ketone; bp. 129°–130° C at 0.5 mm pressure. 7.2 parts of sodium hydride dispersion 55% are suspended three times in benzene and the latter is decanted each time. Then there are added successively 150 parts of hexamethylphosphoramide and dropwise 26.1 parts of diethyl 2-methylmalonate. The mixture is slightly heated and when the reaction is ceased, there are added 36.1 parts of 2-chloro-4-fluorophenyl 2-thienyl ketone. The whole is stirred for 6 hours at 100° C. The reaction mixture is cooled and 320 parts of benzene are added. The organic phase is washed twice with water, dried and evaporated. The residue is distilled, yielding diethyl 2-[3-chloro-4-(2-thenoyl)phenyl]-2-methylmalonate; bp. 225°–235° C at 0.6–0.8 mm pressure.

A mixture of 29.7 parts of diethyl 2-[3-chloro-4-(2-thenoyl)phenyl]-2-methylmalonate and 200 parts of sodium hydroxide solution 5% is stirred and refluxed for 5 hours. The reaction mixture is cooled and washed twice with 80 parts of benzene. The aqueous phase is acidified with concentrated hydrochloric acid solution and the product is extracted with chloroform. The extract is dried, filtered and evaporated. The oily residue is dissolved in 160 parts of ether. This solution is stirred with activated charcoal, filtered and evaporated. The oily residue is purified by column-chromatography, using a mixture of chloroform and 5% of methanol. The pure fractions are collected and the solvent is evaporated. The oily residue which solidifies on standing, is triturated in a mixture of benzene and petroleumether, yielding 3-chloro-4-(2-thenoyl)-hydratropic acid; mp. 82.5° C; also named 3-chloro-4-(2-thenoyl)-α-methyl-phenylacetic acid.

EXAMPLE V

To a stirred and cooled (ice-bath) mixture of 88 parts of nicotinoyl chloride hydrochloride in 400 parts of fluorobenzene are added portionwise 165 parts of aluminium chloride at a temperature between 5° and 10° C. Upon completion, the cooling-bath is removed and the mixture is stirred and refluxed for 6 hours. The reaction mixture is allowed to stand overnight at room temperature and is then poured onto a mixture of crushed ice and hydrochloric acid. After cooling, the layers are separated. The aqueous phase is extracted three times with ether. The combined organic layers are discarded and the aqueous phase is alkalized with a 40% sodium hydroxide solution. The product is extracted several times with chloroform. The extracts are washed twice with water, dried and evaporated. The residue is dissolved in ether. The solution is filtered from insoluble matter and the filtrate is allowed to crystallize upon dilution with petroleumether at −20° C, yielding p-fluorophenyl 3-pyridyl ketone; mp. 74.5° C.

9.6 parts of sodium hydride dispersion 55% are stirred three times in anhydrous benzene and the latter is decanted each time. Then there are added successively 200 parts of hexamethylphosphoramide and in three portions 34.8 parts of diethyl 2-methylmalonate. The mixture is warmed till the reaction is started and there are added 40.2 parts of p-fluorophenyl 3-pyridyl ketone. The whole is stirred for 6 hours at a temperature of about 100° C. The reaction mixture is allowed to stand overnight (about 15 hours) at room temperature. The product is extracted with benzene. The extract is washed with water, dried, filtered and evaporated, yielding diethyl 2-methyl-2-[p-(3-pyridylcarbonyl)-phenyl]malonate as a residue.

60 parts of diethyl 2-methyl-2-[p-(3-pyridylcarbonyl)-phenyl]malonate (residue of previous reaction) are distilled, yielding about 20.3 parts of ethyl p-(3-pyridylcarbonyl)hydratropate, also named ethyl p-(3-pyridylcarbonyl)-α-methyl-phenylacetate, bp. 235°-244° C at >3 mm pressure.

A mixture of 10 parts of ethyl p-(3-pyridylcarbonyl)-hydratropate and 50 parts of sodium hydroxide solution 4% is stirred and refluxed for 6 hours. The reaction mixture is allowed to stand overnight at room temperature. The whole is extracted with ether. The organic layer is discarded and the aqueous phase is acidified with hydrochloric acid solution. The precipitated product is filtered off, washed with ether and suspended in acetone. The suspension is acidified with an excess of 2-propanol previously saturated with gaseous hydrogen chloride. The salt is washed with acetone and dried, yielding p-(3-pyridylcarbonyl)hydratropic acid hydrochloride; mp. 210° C; also named p-(3-pyridylcarbonyl)-α-methyl-phenylacetic acid HCl.

EXAMPLE VI

To a stirred mixture of 29.5 parts of 2-methylthiophene, 39.65 parts of p-fluorobenzoyl chloride and 280 parts of methylene chloride are added portionwise 40 parts of aluminium chloride while keeping the temperature at 20° C (water-bath). Upon completion, stirring is continued for 4 hours at room temperature. The reaction mixture is poured onto crushed ice and 50 parts of hydrochloric acid, while stirring vigorously. The layers are separated and the aqueous phase is washed with chloroform. The organic layers are dried and evaporated. The residue is taken up in benzene and the latter is evaporated again. The residue solidifies on triturating in petroleumether. The solid product is filtered off and crystallized from ethanol at −20° C, yielding p-fluorophenyl 5-methyl-2-thienyl ketone; mp. 68° C.

5.8 parts of sodium hydride dispersion 55% is triturated three times in benzene and the latter is decanted each time. Then there are added 120 parts of hexamethylphosphoramide and the mixture is heated to 40° C. 20.9 parts of diethyl 2-methylmalonate are added dropwise (slowly) and when the reaction ceases, there are added 26.4 parts of p-fluorophenyl 5-methyl-2-thienyl ketone. The whole is stirred for 7 hours at 100° C. The reaction mixture is cooled, washed with water, dried and evaporated. The residue is distilled, yielding 15.5 parts of diethyl 2-methyl-2-[p-(5-methyl-2-thenoyl)-phenyl]malonate; bp. 235°-240° C at 1 mm pressure.

A mixture of 15.5 parts of diethyl 2-methyl-2-[p-(5-methyl-2-thenoyl)phenyl]malonate and 120 parts of sodium hydroxide solution 5% is stirred and refluxed for 5 hours. The reaction mixture is cooled and shaken twice with 80 parts of benzene. The aqueous phase is acidified with concentrated hydrochloric acid solution. After standing for 10 minutes, the product is extracted with chloroform. The extract is washed with water, dried, filtered and evaporated. The residue is triturated in petroleumether. The crude product is filtered off and purified by column-chromatography using a mixture of chloroform and 10% of methanol. The pure fractions are collected and the solvent is evaporated. The residue is crystallized from acetonitrile at −20°0 C, yielding p-(5-methyl-2-thenoyl)hydratropic acid; mp. 93.7° C.

EXAMPLE VII 2.4 parts of sodium hydride dispersion 50% are washed while stirring in dry benzene (three times) and the benzene is decanted each time. It is then suspended in 125 parts of dry hexamethylphosphoramide and there are added 8.7 parts of diethyl 2-methylmalonate. The whole is warmed and when the reaction is started, there are added 12.7 parts of p-fluorophenyl 2-naphthyl ketone. The whole is stirred for 6 hours at 100° C. The reaction mixture is poured onto a mixture of benzene and water. The organic layer is separated, washed with water, dried, filtered and evaporated. The oily residue is purified by columnchromatography, using benzene and methanol 5% as eluent. The pure fractions are collected and the solvent is evaporated, yielding diethyl 2-methyl-2-[p-(2-naphthoyl)-phenyl]malonate as a residue.

A mixture of 9.1 parts of diethyl 2-methyl-2-[p-(2-naphthoyl)phenyl]malonate, 6 parts of sodium hydroxide and 150 parts of water is stirred and refluxed for 8 hours. The reaction mixture is allowed to stand overnight at room temperature. The whole is diluted with water and the product is extracted with ether. The organic layer is separated and discarded. The aqueous phase is degassed on a rotavapor, filtered and acidified with hydrochloric acid solution; an oil is separated which solidifies on standing. The latter is extracted with ether and the extract is washed with water, dried and evaporated. The residue is crystallized from acetonitrile. The product is filtered off, washed with acetonitrile and dried, yielding p-(2-naphthoyl)hydratropic acid; m.p. 149.7° C.

EXAMPLE VIII

A mixture of 20 parts of m-bromo-α-methylbenzylalcohol and 16.8 parts of 3,4-dihydropyran is cooled in an ice-bath and there are added 2 drops of hydrochloric acid solution. The whole is stirred overnight at 0° C and then allowed to come to room temperature. The mixture is poured onto ether and shaken successively with a sodium hydrogen carbonate solution and twice with water. The organic layer is separated, dried, filtered and evaporated. The residue is distilled, yielding 2-(m-bromo-α-methylbenzyloxy)tetrahydropyran; bp. 168°-169° C at 12 mm. pressure.

To a stirred and refluxing Grignard complex, previously prepared starting from 2.4 parts of magnesium and 31.3 parts of 2-(m-bromo-α-methylbenzyloxy)tetrahydropyran in 70 parts of tetrahydrofuran, is added dropwise a solution of 10.9 parts of 2-thiophenecarbonitrile in 20 parts of tetrahydrofuran. Upon completion, stirring at reflux is continued for 3.5 hours. The reaction mixture is cooled to about 15° C and treated with 50 parts of a saturated ammonium chloride solution. The whole is extracted with water and ether. The organic phase is washed thoroughly with water, dried and acidified with hydrochloric acid in 2-propanol. The precipitated product is filtered off and dissolved in 100 parts of water and 50 parts of concentrated hydrochloric acid solution. The solution is stirred with charcoal, filtered and the filtrate is then stirred at reflux temperature for 10 minutes, whereupon the product is separated as an oil. After cooling, the product is extracted with ether. The latter is washed with water, dried and evaporated, yielding α-hydroxy-α-methyl-m-tolyl-2-thienyl ketone as a residue.

5.5 parts of thionyl chloride is added dropwise to a stirred solution of 9.5 parts of α-hydroxy-α-methyl-m-tolyl 2-thienyl ketone in 40 parts of benzene while keeping the temperature below 20° C. Upon completion, stirring is continued for one hour at room temperature and for one additional hour at 30°-35° C. The reaction mixture is evaporated in vacuo. The residue is taken up in toluene and the latter is evaporated again. The residue is distilled, yielding α-chloro-α-methyl-m-tolyl 2-thienyl ketone; bp. 168°-178° C at 0.7 mm pressure.

To a stirred and hot mixture of 2.7 parts of sodium cyanide in 20 parts of dimethylsulfoxide is added dropwise a solution of 5.8 parts of α-chloro-α-methyl-m-tolyl 2-thienyl ketone in 10 parts of dimethylsulfoxide at 60° C. Another 5 parts of dimethylsulfoxide is added and the whole is stirred for 2.5 hours at 50°–55° C. The reaction mixture is poured onto 35 parts of water and the product is extracted with ether and ethyl acetate. The combined organic layers are washed with water, dried, filtered and evaporated in vacuo. The residue is dissolved in benzene. This solution is washed with water, dried and evaporated in vacuo, yielding m-(2-thenoyl)hydratroponitrile, also named α-cyano-α-methyl-m-tolyl 2-thienyl ketone, as a residue.

To 5 parts of water are added dropwise 9 parts of concentrated sulfuric acid, followed by the addition of a solution of 5 parts of m-(2-thenoyl)hydratroponitrile in 5 parts of glacial acetic acid. Upon completion, the whole is stirred at gentle reflux temperature for 2 hours (oilbath at 120° C). The reaction mixture is cooled, poured onto crushed ice and the product is extracted with ether. The organic layer is washed with water and the aqueous phase is discarded. The organic phase is washed with 5% sodium hydroxide solution (twice: 50 and 25 parts resp.). The alkaline aqueous phase is washed with ether and acidified with concentrated hydrochloric acid solution: an oil is separated. The latter is extracted with ether. The extract is dried and evaporated. The residue is dissolved in 20 parts of ether and 20 parts of petroleumether, whereupon an oil is separated. The solvent is decanted (the oil is discarded) and evaporated, yielding m-(2-thenoyl)hydratropic acid as a residue.

EXAMPLE IX

A. 4.55 parts of sodium hydride dispersion 55% are washed three times with anhydrous benzene and the latter is decanted each time. The sodium hydride dispersion 55% is mixed with 100 parts of dry hexamethylphosphoramide and there are added 18.8 parts of diethyl 2-ethylmalonate in three portions. When the reaction is complete (hydrogen is evolved), there are added 20.6 parts of p-fluorophenyl 2-thienyl ketone and the whole is stirred for 20 hours at 100° C. The reaction mixture is cooled and poured onto benzene. The organic layer is shaken with water, dried, filtered and evaporated. The residue is distilled, yielding diethyl 2-ethyl-2-[p-(2-thenoyl)phenyl]malonate; bp. 175°–199° C at 0.1 mm pressure.

A mixture of 16.8 parts of diethyl 2-ethyl-2-[p-(2-thenoyl)phenyl]malonate, 4 parts of sodium hydroxide and 80 parts of water is stirred and refluxed for 6 hours. The reaction mixture is poured onto water and the whole is extracted with ether. The aqueous phase is separated and acidified with hydrochloric acid solution; the product is separated as an oil which solidifies. It is extracted with ether. The extract is washed three times with water, dried, filtered and evaporated. The solid residue is crystallized from 24 parts of acetonitrile at room temperature, yielding 2-[p-(2-thenoyl)phenyl]-butyric acid, also named p-(2-thenoyl)-α-ethyl-phenylacetic acid; mp. 122.8° C.

B. By repeating the procedure of Example IX-A, except that an equivalent amount of an appropriate p-fluorophenyl aryl ketone is initially employed, the following respective products are obtained:
p-(2-naphthoyl)-α-ethyl-phenylacetic acid;
p-(5-methyl-2-thenoyl)-α-ethyl-phenylacetic acid; and
p-(3-pyridylcarbonyl)-α-ethyl-phenylacetic acid.

EXAMPLE X

A. 6 parts of sodium hydride dispersion 55% are triturated three times in anhydrous benzene and the latter is decanted each time. The sodium hydride dispersion is taken up in 125 parts of dry hexamethylphosphoramide and there are added dropwise 25 parts of diethyl 2-allylmalonate (exothermic reaction). Upon completion, the whole is stirred for 30 minutes. When the reaction ceases, there are added 25.8 parts of p-fluorophenyl 2-thienyl ketone and the whole is stirred for 7 hours at 100° C. The reaction mixture is cooled and 400 parts of benzene are added. The organic phase is separated, washed three times with water, dried and evaporated. The oily residue is distilled, yielding diethyl 2-allyl-2-[p-(2-thenoyl)phenyl]malonate; bp. 215°–220° C at 0.2 mm pressure.

A mixture of 20.3 parts of diethyl 2-allyl-2-[p-(2-thenoyl)phenyl]malonate and 150 parts of sodium hydroxide solution 5% is stirred and refluxed for 5 hours. The reaction mixture is cooled and washed twice with 80 parts of ether. The aqueous phase is separated and acidified with concentrated hydrochloric acid solution till strongly acid; an oil is separated which solidifies. The product is extracted with ether. The extract is washed with water, dried and evaporated. The oily residue solidifies on triturating in petroleumether. The solid product is filtered off and crystallized from 32 parts of acetonitrile at −20° C, yielding 2-[p-(2-thenoyl)phenyl]-4-pentenoic acid; mp. 117.1° C; also named p-(2-thenoyl)-α-allyl-phenylacetic acid.

B. The procedure of Example X-A is repeated, except that an equivalent quantity of an appropriate p-fluorophenyl aryl ketone is initially employed, to yield the following respective products:
p-(3-pyridylcarbonyl)-α-allyl-phenylacetic acid;
p-(5-methyl-2-thenoyl)-α-allyl-phenylacetic acid; and
p-(2-naphthoyl)-α-allyl-phenylacetic acid.

EXAMPLE XI

The following esters of formula (I) are obtained as respective products by repeating the esterification procedure of Example II, except that an equivalent amount of an appropriate aroyl-substituted phenylacetic acid is used:
ethyl p-(2-thenoyl)-α-allyl-phenylacetate;
ethyl p-(2-thenoyl)-α-ethyl-phenylacetate;
ethyl m-(2-thenoyl)-α-methyl-phenylacetate;
ethyl p-(2-naphthoyl)-α-methyl-phenylacetate;
ethyl p-(5-methyl-2-thenoyl)-α-methyl-phenylacetate;
ethyl 3-chloro-4-(2-thenoyl)-α-methyl-phenylacetate.

EXAMPLE XII

By repeating the esterification procedure of Example III, except that an equivalent amount each of an appropriate aroyl-substituted phenylacetic acid and an appropriate alkyl halide are utilized, the following esters of formula (I) are obtained as respective products:
propyl p-(2-thenoyl)-α-allyl-phenylacetate;
butyl p-(2-thenoyl)-α-ethyl-phenylacetate;
octyl m-(2-thenoyl)-α-methyl-phenylacetate;
propyl p-(2-naphthoyl)-α-methyl-phenylacetate; and
pentyl 3-chloro-4-(2-thenoyl)-α-methyl-phenylacetate.

EXAMPLE XIII

The procedure of Example VIII is followed except that an equivalent amount of an appropriate aryl nitrile is used in place of the 2-thiophenecarbonitrile used therein to yield, as respective products, the following: m-(2-naphthoyl)hydratropic acid; m-(5-methyl-2-thenoyl)hydratropic acid; and m-(3-pyridylcarbonyl)hydratropic acid.

EXAMPLE XIV

A mixture of 7.3 parts of p-(2-thenoyl)hydratroponitrile, 18 parts of sulfuric acid, 10 parts of water and 10 parts of acetic acid is stirred and refluxed for 2 hours. The reaction mixture is poured onto crushed ice and the product is extracted with ether. The organic layer is washed with diluted sodium hydroxide solution. The aqueous phase is acidified with hydrochloric acid solution and the product is extracted with ether. The organic layer is dried, stirred with activated charcoal, filtered and evaporated in vacuo. The residue solidifies on triturating in petroleumether. The solid product is filtered off and crystallized from acetonitrile, yielding p-(2-thenoyl)hydratropic acid; mp. 121.1° C.

EXAMPLE XV

To a stirred mixture of 20 parts of p-(2-thenoyl)hydratropic acid and 9.3 parts of (-)-α-methylbenzylamine in 200 parts of ethanol are added 50 parts of water. The precipitated salt is filtered off and crystallized from a mixture of ethanol and water (10 : 2 by volume), yielding the crude salt form. This fraction is recrystallized several times till constant rotation, from a mixture of ethanol and water (10 : 2 by volume), to yield (-)-p-(2-thenoyl)hydratropic acid α-methylbenzylamine; m.p. 170.5° C.; $[\alpha]$ (1.98% MeOH) = $-13.74°$.

1.5 Parts of (-)-p-(2-thenoyl)hydratropic acid α-methylbenzylamine are suspended in water and acidified with hydrochloric acid. The product is extracted with ether. The organic layer is washed with water, dried and evaporated. The oily residue solidifies on triturating in petroleumether. The solidified product is filtered off and dried in vacuo at 50° C, yielding (+)-p-(2-thenoyl)hydratropic acid; $[\alpha]$ (1% in MeOH) = +44.5°.

EXAMPLE XVI

To a stirred mixture of 30 parts of p-(2-thenoyl)hydratropic acid and 14 parts of (+)-α-methylbenzylamine in 200 parts of ethanol are added 50 parts of water. The precipitated salt is filtered off and crystallized from a mixture of ethanol and water (10 : 2 by volume), yielding the crude salt form. This fraction is recrystallized several times till constant rotation, from a mixture of ethanol and water (10 : 2 by volume), yielding (+)-p-(2-thenoyl)hydratropic acid α-methylbenzylamine; mp. 171.1° C.; $[\alpha]$ (2.02% MeOH) = +13.55°.

1 part of (+)-p-(2-thenoyl)hydratropic acid α-methylbenzylamine is suspended in water and acidified with hydrochloric acid. The product is extracted with ether. The organic layer is washed with water, dried, filtered and evaporated in vacuo. The oily residue solidifies on triturating in petroleumether. The solidified product is filtered off and dried in vacuo at 50° C, yielding (-)-p-(2-thenoyl)hydratropic acid; $[\alpha]$ (1% MeOH) = -45.6°.

EXAMPLE XVII

To a stirred mixture of 29.2 parts of 2-thenoyl chloride, 22 parts of m-fluorotoluene and 200 parts of methylene chloride are added portionwise 37.4 parts of aluminum chloride (exothermic reaction: temperature rises to 30° C). Upon completion, stirring is continued for 3 hours at reflux temperature. The reaction mixture is poured onto crushed ice while stirring. The product is extracted with methylene chloride. The organic phase is washed successively with a sodium hydrogen carbonate solution and with water, dried and evaporated. The residue is distilled twice, yielding 4-fluoro-o-tolyl 2-thienyl ketone; bp. 105°-106° C at 0.2 mm. pressure.

2.3 parts of sodium hydride dispersion 78% are suspended three times in anhydrous benzene and the latter is decanted each time. A vessel is filled with 65 parts of hexamethylphosphoramide and 2.3 parts of sodium hydride dispersion 78% are added, followed by the addition of 14.5 parts of diethyl 2-methylmalonate (exothermic reaction: temperature rises to 58° C). Upon completion, stirring is continued for 3h. 30. Then there are added dropwise 14 parts of 4-fluoro-o-tolyl 2-thienyl ketone while heating till a temperature of 100°-110° C is reached. The whole is stirred at this temperature for 7 hours. The product is extracted with benzene. The extract is washed three times with water, dried, filtered and evaporated. The residue is distilled, yielding diethyl 2-methyl-2-[4-(2-thenoyl)m-tolyl]malonate; bp. 186°-193° C at 0.2 mm. pressure.

A mixture of 5.8 parts of diethyl 2-methyl-2-[4-(2-thenoyl)m-tolyl]malonate, 33.7 parts of sodium hydroxide solution 5% and 4parts of ethanol is stirred and refluxed for 7 hours. The reaction mixture is cooled to room temperature and washed twice with benzene. The aqueous phase is acidified with concentrated hydrochloric acid solution, whereupon an oil is separated. The product is extracted with chloroform (twice). The extract is dried, filtered and evaporated. The oily residue is purified by column-chromatography over silicagel, using a mixture of chloroform and 5% of methanol as eluent. The pure fractions are collected and the eluent is evaporated. The residue is crystallized from-n-hexane, yielding 3-methyl-4-(2-thenoyl)hydratropic acid; mp. 100.2° C.

EXAMPLE XVIII

To a stirred and refluxing Grignard-complex, previously prepared starting from 7.2 parts of magnesium and 81.4 parts of 2-(p-bromobenzyloxy)tetrahydropyran in 200 parts of dry tetrahydrofuran, is added dropwise a solution of 32.7 parts of 2-thiophenecarbonitrile in 70 parts of dry tetrahydrofuran (exothermic reaction: reflux temperature is maintained). Upon completion, stirring at reflux is continued for 4 hours. The reaction mixture is cooled and decomposed with 150 parts of a saturated ammonium chloride solution at about 15° C. The whole is poured onto water and the product is extracted with ether. The organic layer is washed four times with water, dried, filtered and acidifed with gaseous hydrogen chloride: an oil is separated. The ether is decanted and the oily product is dissolved in 300 parts of water and 150 parts of concentrated hydrochloric acid solution. The solution is stirred with activated charcoal, filtered and the filtrate is stirred and refluxed for 10 minutes. The product is extracted with chloroform. The latter is washed with water, dried, filtered and evaporated. The residue is distilled, yielding α-hydroxy-p-tolyl 2-thienyl ketone; bp. 180°-190° C at 0.2 mm. pressure.

To a stirred and cooled suspension of 31 parts of α-hydroxy-p-tolyl 2-thienyl ketone in 160 parts of dry benzene are added dropwise 24 parts of thionyl chloride at 10° C. Upon completion, stirring is continued overnight at room temperature. The reaction mixture is evaporated and the residue is evaporated twice more from toluene. The latter residue is triturated in petroleumether. The product is filtered off and dissolved in 320 parts of ether. This solution is stirred with charcoal, filtered and the filtrate is evaporated. The residue is crystallized from ethanol at −20° C, yielding α-chloro-p-tolyl 2-thienyl ketone.

A mixture of 5.9 parts of sodium cyanide in 40 parts of dimethyl sulfoxide is heated to 60° C and there are added at once 9.5 parts of α-chloro-p-tolyl 2-thienyl ketone (exothermic reaction: temperature rises to 100° C). The whole is stirred for 2 hours at 60° C. After cooling, the reaction mixture is poured onto water and the product is extracted three times with 450 parts of chloroform. The combined extracts are washed twice with 200 parts of water, dried and evaporated. The dark-coloured residual tar is extracted five times with ether; the combined ether extracts are stirred with activated charcoal, filtered and evaporated. The residue is triturated in petroleumether (solid carbon dioxide) and the whole is evaporated, yielding 2-[p-(2-thenoyl)-phenyl]acetonitrile as a residue.

To a stirred mixture of 5.5 parts of sodium hydride dispersion 78% in 150 parts of hexamethylphosphoramide are added dropwise 14 parts of 2-[p-(2-thenoyl)-phenyl]acetonitrile over a period of 30 minutes at a temperature of 15° C. Upon completion, stirring is continued for 3 hours at room temperature. Then there are added dropwise 34 parts of methyl iodide (strong exothermic reaction) and upon completion, the whole is stirred overnight. The reaction mixture is poured onto water and the product is extracted three times with 200 parts of benzene. The combined extracts are washed five times with water, dried, filtered and evaporated, yielding α-methyl-p-(2-thenoyl)hydratroponitrile as a residue.

A mixture of 14.5 parts of α-methyl-p-(2-thenoyl)hydratroponitrile, 38 parts of sulfuric acid 98%, 20 parts of acetic acid and 20 parts of water is stirred and refluxed for 2h. 30. The reaction mixture is poured onto ice-water and extracted with ether. The ether-phase is extracted with diluted sodium hydroxide solution, washed with ether and acidified with diluted hydrochloric acid solution. The aqueous layer is extracted with ether and treated with charcoal. The extract is dried, filtered and evaporated. The residue is evaporated once more from benzene. The latter residue is triturated in petroleumether. The solid product is filtered off and crystallized from 2-propanol, yielding, after drying, α-methyl-p-(2-thenoyl)hydratropic acid; mp. 138.8° C.

EXAMPLE XIX

To a stirred and refluxing Grignard-complex, previously prepared starting from 7.3 parts of magnesium, 52.6 parts of methyl iodide in 160 parts of ether, is added dropwise a solution of 19.6 parts of 3'-bromo-2'-methylbenzonitrile in 40 parts of ether. Upon completion, stirring at reflux is continued for 20 hours. The reaction mixture is cooled to 0° C and poured onto 500 parts of ice-water while stirring vigorously. The ethereal phase is separated, dried and evaporated. The residue is boiled in 60 parts of a 6N hydrochloric acid solution for 10 minutes. The separated oil is extracted with ether. The extract is washed with water, dried and evaporated. The residue is distilled, yielding 3'-bromo-2'-methylacetophenone; bp. 125°–128° C at 10 mm. pressure.

A mixture of 100 parts of 3'-bromo-2'-methylacetophenone, 30 parts of ethylene glycol, 320 parts of anhydrous toluene and 2 parts of p-toluenesulfonic acid is stirred and refluxed for 4 hours with water-separator. A second fraction of 30 parts of ethylene glycol is added and stirring at reflux is continued for 18 hours. The reaction mixture is cooled and stirred for 30 minutes with 5 parts of sodium carbonate. The organic layer is separated, washed twice with water, dried and evaporated. The residue is distilled twice, yielding 2-(3-bromo-o-tolyl)-2-methyl-1,3-dioxolane; bp. 148°–150° C at 12 mm. pressure.

To a stirred and refluxing Grignard-complex, previously prepared starting from 72 parts of 2-(3-(bromo-o-tolyl)-2-methyl-1,3-dioxolane, 6.8 parts of magnesium and 180 parts of dry tetrahydrofuran, is added dropwise a solution of 30.6 parts of 2-thenonitrile in 90 parts of dry tetrahydrofuran. Upon completion, stirring at reflux is continued for 2 hours. The reaction mixture is allowed to stirr overnight at room temperature. After cooling to 0° C, the mixture is decomposed by the addition of 200 parts of a saturated ammonium chloride solution while keeping the temperature below 20° C. The product is extracted with 1200 parts of ether. The extract is washed three times with 300 parts of water and upon saturation of the ether-phase with gaseous hydrogen chloride, the ketimine-compound is separated as an oil. The ether is decanted and the oil is stirred and refluxed for 3 hours in 500 parts of a 6N hydrochloric acid solution. After cooling, the product is extracted with chloroform (2 × 225 parts). The extract is dried and evaporated. The residue is distilled twice, yielding 2'-methyl-3'-(2-thenoyl)acetophenone; bp. 185°–190° C at 0.4 mm. pressure.

A mixture of 14.7 parts of 2'-methyl-3'-(2-thenoyl-)acetophenone, 4.3 parts of sulfur and 33 parts of morpholine is stirred and refluxed for 3 hours. The reaction mixture is cooled, diluted with 450 parts of chloroform and shaken successively twice with diluted hydrochloric acid solution and twice with water. The organic layer is dried and evaporated. The oily residue is boiled in a mixture of 200 parts of glacial acetic acid and 150 parts of a 50% sulfuric acid solution for 2 hours. After cooling, the mixture is poured onto 700 parts of ice-water and the product is extracted twice with ether. The combined extracts are washed with water, dried, stirred with activated charcoal, filtered and evaporated. The residue is taken up in 200 parts of water, alkalized with diluted sodium hydroxide solution and washed twice with ether. The aqueous phase is acidified with concentrated hydrochloric acid solution and the product is extracted twice with ether. The extracts are dried and evaporated. The residue is purified by column-chromatography over silica gel, using a mixture of chloroform and 5% of methanol as eluent. The pure fractions are collected and the eluent is evaporated. The residue is dissolved in ether and the solution is stirred with activated charcoal. The latter is filtered off and the filtrate is evaporated. The residue is crystallized from acetonitrile at −20° C, yielding a 2-[3-(2-thenoyl)-o-tolyl]acetic acid; m.p. 136° C.

EXAMPLE XX

A mixture of 26 parts of 5-chloro-2-thienyl p-ethylphenyl ketone, 350 parts of carbon tetrachloride, 1 part of benzoyl peroxide and 18.5 parts of N-bromosuccinimide is stirred and refluxed. When the reaction ceased, the formed precipitate is filtered off and the carbon tetrachloride phase is dried and evaporated. The residue solidifies on cooling on ice. The solid product is crystallized from 2-propanol (activated charcoal), yielding, after drying in vacuo, α-bromo-α-methyl-p-tolyl 5-chloro-2-thienyl ketone; mp. 69.4° C.

A mixture of 9.9 parts of α-bromo-α-methyl-p-tolyl 5-chloro-2-thienyl ketone, 1.96 parts of sodium cyanide, 12 parts of water and 48 parts of dioxane is stirred for 17 hours while heating at 90° C. The reaction mixture is evaporated and 36 parts of water are added to the residue. The product is extracted with ether. The extract is dried and evaporated. The residue is purified by column-chromatography over silica gel, using chloroform as eluent. The pure fraction is collected and the eluent is evaporated. The residue is triturated in n-hexane, yielding p-(5-chloro-2-thenoyl)hydratroponitrile; mp. 90° C.

To a stirred mixture of 4.2 parts of water, 4.2 parts of acetic acid and 7.4 parts of concentrated sulfuric acid 98% are added 4.2 parts of p-(5-chloro-2-thenoyl)hydratroponitrile. The whole is heated to reflux and stirred at reflux temperature for 4h. 30. The reaction mixture is poured onto ice-water and the product is extracted with ether. The organic layer is washed with a 5% sodium hydroxide solution. The aqueous phase is acidified with concentrated hydrochloric acid solution and extracted with ether. The combined ether extracts are washed twice with water, dried, filtered and the filtrate is stirred with charcoal. The latter is filtered off and the filtrate is evaporated. The residue is crystallized from acetonitrile, yielding p-(5-chloro-2-thenoyl)hydratropic acid; mp. 137.4° C.

EXAMPLE XXI

A mixture of 5.2 parts of p-(2-thenoyl)hydratropic acid, 4.8 parts of thionyl chloride and 32 parts of anhydrous benzene is stirred and refluxed for 3h. 30. The reaction mixture is evaporated and the residue is evaporated once more from benzene, yielding p-(2-thenoyl)hydratropoyl chloride as a residue.

To a solution of 3.7 parts of p-methoxyaniline in 20 parts of dioxane, is added a solution of 4.2 parts of p-(2-thenoyl)hydratropoyl chloride in 25 parts of dioxane. Upon completion, another 30 parts of dioxane are added and the whole is stirred and refluxed for one hour. The reaction mixture is allowed to cool to room temperature. After filtration, the filtrate is treated with activated charcoal, filtered and evaporated in vacuo. The oily residue solidifies on triturating in ether. The solid product is filtered off, stirred twice in ether and filtered again. The product is crystallized from 2-propanol, yielding, after drying in vacuo, p-(2-thenoyl)hydratropo-p-anisidide; mp. 149° C.

EXAMPLE XXII

To a stirred and refluxing solution of 3.06 parts of 2-amino-2-thiazoline in 60 parts of dioxane is added a solution of 4.2 parts of p-(2-thenoyl)hydratropoyl chloride in 45 parts of dioxane. Upon completion, stirring at reflux is continued for 30 minutes. The reaction mixture is cooled, filtered and the filtrate is evaporated. The residue is purified by column-chromatography over silicagel, using a mixture of chloroform and 5% of methanol as eluent. The pure fractions are collected and the eluent is evaporated. The residue is crystallized from ethanol, yielding N-(2-thiazolin-2-yl)-p-(2-thenoyl)hydratropamide; mp. 186.4° C.

EXAMPLE XXIII

To a stirred solution of 12.6 parts of ethyl p-(2-thenoyl)hydratropate in 35 parts of methanol is added successively and while cooling, first a solution of 6.05 parts of hydroxyl amine hydrochloride in 35 parts of methanol and then a solution of 7.3 parts of potassium hydroxide in 35 parts of methanol. Upon completion, the whole is stirred for 30 minutes. The mixture is filtered and the filtrate is stirred for 3 days at room temperature. The reaction mixture is evaporated and the residue is taken up in water. The aqueous solution is acidified with hydrochloric acid solution and the product is extracted with ether. The extract is washed with water, dried, filtered and evaporated. The residue is taken up in water, alkalized with sodium hydroxide solution, washed with ether and the aqueous phase is acidified with concentrated hydrochloric acid solution. The product is extracted with ether. The latter is washed with water, dried, filtered and evaporated. The residue is purified by column-chromatography over silicagel, using a mixture of chloroform and 10% of methanol as eluent. The pure fractions are collected and the eluent is evaporated. The residue is triturated in a mixture of petroleumether and diisopropylether. The solid product is filtered off and crystallized from 2-propanol, yielding p-(2-thenoyl)hydratropohydroxamic acid; mp. 143.5° C.

EXAMPLE XXIV 1.3 parts of sodium hydride dispersion 78% are suspended three times in anhydrous benzene and the latter is decanted each time. Then there are added 75 parts of hexamethylphosphoramide, followed by the addition of 10.4 parts of p-(2-thenoyl)hydratropic acid. The whole is heated to 50° C and when the reaction is ceased (formation of sodium salt), the mixture is cooled to room temperature. 7 parts of N-(2-chloroethyl)-N,N-dimethylamine are added and the whole is stirred for 18 hours at 50° C. The reaction mixture is cooled and extracted with 240 parts of benzene. The organic layer is washed successively with 100 parts of water, with diluted sodium hydroxide solution and again with 100 parts of water, dried, filtered and evaporated. The residue is purified twice by column-chromatography over silicagel, using as eluent chloroform the first time and further a mixture of chloroform and 5% of methanol. After evaporation of the eluent, the residue is converted into the oxalate salt in 2-propanol. The crude salt is filtered off and crystallized from 2-propanol (activated charcoal) at −20° C, yielding 2-(dimethylamino)ethyl p-(2-thenoyl)hydratropate oxalate; mp. 117.4° C.

EXAMPLE XXV

A mixture of 10.4 parts of p-(2-thenoyl)hydratropic acid in 75 parts of hexamethylphosphoramide is heated to 50° C and there are added 1.3 parts of sodium hydride dispersion 78.3%. When the reaction is ceased, there are added 10 parts of N-(3-chloropropyl)-N,N-dimethyl amine. The whole is stirred overnight at 50° C. The reaction mixture is cooled and extracted with 240 parts of benzene and 100 parts of water. The organic phase is washed successively with 100 parts of diluted sodium hydroxide solution and with 100 parts of water, dried and evaporated. The oily residue is triturated twice in petroleumether. The latter is decanted and the residue is converted into the oxalate salt in 2-propanol. The solid salt is filtered off and crystallized from 120 parts of 2-propanol (activated charcoal) at room temperature, yielding 3-(dimethylamino)propyl p-(2-thenoyl)hydratropate oxalate; m.p. 135°–145° C.

EXAMPLE XXVI

A mixture of 10.4 parts of p-(2-thenoyl)hydratropic acid in 75 parts of hexamethylphosphoramide is heated to 50° C and there are added 1.3 parts of sodium hydride dispersion 78.3%. When the reaction is ceased, there are added 10 parts of N-(2-chloroethyl)-N,N-diethylamine and the whole is stirred overnight at 50° C. The reaction mixture is cooled and extracted with 240 parts of benzene and 100 parts of water. The organic layer is washed with diluted sodium hydroxide solution and with water, dried and evaporated. The oily residue is converted into the hydrochloride salt in 2-propanol. After cooling to −20° C, the precipitated salt is filtered off and dried, yielding 2-(diethylamino)ethyl p-(2-thenoyl)hydratropate hydrochloride; mp. 126.4° C.

EXAMPLE XXVII

To a stirred and cooled (0° C) mixture of 4.2 parts of thiophene, 13 parts of stannic chloride and 40 parts of methylene chloride is added dropwise a solution of 11.7 parts of p-(bromomethyl)benzoyl chloride in 16 parts of methylene chloride (exothermic reaction with gaseous hydrogen chloride evolution). After stirring for 2h. 30, the reaction mixture is poured onto a mixture of 20 parts of hydrochloric acid solution and 100 parts of crushed ice. The product is extracted with methylene chloride. The organic phase is washed with alkaline water, dried and evaporated. The solid residue is triturated with hot petroleumether. The product is filtered off and crystallized from ethanol, yielding α-bromo-p-tolyl-2-thienyl ketone; mp. 85.6° C (dec.).

A mixture of 5.9 parts of sodium cyanide in 40 parts of dimethyl sulfoxide is heated to 60° C and there are added at once 11.3 parts of α-bromo-p-tolyl 2-thienyl ketone (exothermic reaction: temperature rises to 100° C). The whole is stirred for 2 hours at 60° C. After cooling, the reaction mixture is poured onto water and the product is extracted three times with 450 parts of chloroform. The combined extracts are washed twice with 200 parts of water, dried and evaporated. The dark-coloured residual tar is extracted several times with ether. The combined ether extracts are stirred with activated charcoal, filtered and evaporated. The residue is triturated in petroleumether (solid carbon dioxide) and the whole is evaporated, yielding 2-[p-(2-thenoyl)-phenyl]acetonitrile as a residue.

A mixture of 8.6 parts of 2-[p-(2-thenoyl)phenyl]-acetonitrile, 18 parts of concentrated sulfuric acid, 10 parts of acetic acid and 10 parts of water is stirred and refluxed for one hour. The reaction mixture is cooled and poured onto 200 parts of ice-water. The product is extracted twice with 160 parts of ether. The combined extracts are washed with 100 parts of diluted sodium hydroxide solution and separated. The aqueous phase is acidified with concentrated hydrochloric acid solution, whereupon the product is separated as an oil. The latter is extracted with ether. The extract is dried and evaporated. The residue is triturated in petroleumether and the crude product is dissolved in chloroform. It is purified by column chromatography, using a mixture of chloroform and 5% of methanol. The pure fractions are collected and the solvent is evaporated. The residue is triturated in petroleumether and the solid product is crystallized from acetonitrile at −20° C, yielding 2-[p-(2-thenoyl)phenyl]acetic acid; mp. 126°–129° C.

To 400 parts of liquid ammonia are added a trace of ferric chloride and 3 parts of sodium. The mixture is stirred for 30 minutes, after which 14.8 parts of 2-[p-(2-thenoyl)phenyl]acetic acid are added slowly during 30 minutes, and the mixture is further stirred for 45 minutes. 13.6 parts of methyl iodide are added dropwise and the reaction mixture is stirred for 2h. 30 400 parts of diethyl ether are then added and the mixture is stirred overnight. The ammonia is evaporated and the resulting solution is acidified with diluted hydrochloric acid. The ethereal layer is separated and extracted with 10% sodium hydroxide solution. The extract is washed with ether, acidified and extracted with ether. The ethereal solution is dried on sodium sulfate and the ether is evaporated in vacuo. The residue is triturated in petroleumether, filtered off and crystallized twice from acetonitrile, first at −20° C and then at 0° C, yielding p-(2-thenoyl)hydratropic acid.

EXAMPLE XXVIII

To a stirred mixture of 26.7 parts of p-ethylbenzoyl chloride, 13.3 parts of thiophene in 80 parts of methylene chloride are added 41.1 parts of stannic chloride in 40 parts of methylene chloride at 30° C. Upon completion, stirring is continued for 3h.30 at reflux temperature. The reaction mixture is poured onto a mixture of crushed ice and hydrochloric acid. The layers are separated and the aqueous phase is extracted with methylene chloride. The combined organic layers are washed with water, dried, filtered and evaporated. The residue is evaporated once more from benzene. The latter residue is distilled, yielding p-ethylphenyl 2-thienyl ketone; bp. 200–205° C at 12 mm. pressure.

A mixture of 23.5 parts of p-ethylphenyl 2-thienyl ketone, 19.5 parts of N-bromosuccinimide, 220 parts of carbon tetrachloride, 1.1 parts of benzoyl peroxide and one drop of toluene is stirred and refluxed for 2 hours. The precipitated succinimide is filtered off and the carbon tetrachloride filtrate is dried and evaporated. The oily residue solidifies on cooling. The solid product is dissolved in 2-propanol and the product is allowed to crystallize. It is filtered off and dried in vacuo, yielding α-bromo-α-methyl-p-tolyl 2-thienyl ketone; mp. 71.1° C.

A suspension of 4.9 parts of sodium cyanide in 55 parts of dimethyl sulfoxide is stirred while heating to 60° C. Then there are added at once 10 parts of α-bromo-α-methyl-p-tolyl 2-thienyl ketone and stirring at 60° C is continued for 4h.30. The reaction mixture is poured onto water and the product is extracted with ether. The organic layer is washed with water, dried, filtered and evaporated, yielding p-(2-thenoyl)hydratroponitrile as a residue.

EXAMPLE XXIX

A mixture of 269 parts of p-bromo-α-methylbenzyl alcohol and 225 parts of 2H-3,4-dihydropyran is stirred and cooled to 0° C. Then there are added dropwise 10 drops of concentrated hydrochloric acid solution and the whole is stirred in an ice-bath (room temperature is reached). After stirring for 24 hours, the reaction mixture is poured onto 1200 parts of ether. The organic phase is washed twice with a sodium hydrogen carbonate solution and twice with water, dried, filtered and evaporated. The residue is distilled, yielding 2-(p- bromo-α-methylbenzyloxy)tetrahydropyran; bp. 165°–177° C. at 20 mm. pressure.

A Grignard-complex is formed starting from 7.2 parts of magnesium and 93.9 parts of 2-(p-bromo-α-methylbenzyloxy)tetrahydropyran in 200 parts of dry tetrahydrofuran. To this stirring and refluxing complex is added dropwise a solution of 32.7 parts of 2-thiophenecarbonitrile in 70 parts of dry tetrahydrofuran and stirring at reflux is continued for 4 hours. The reaction mixture is stirred overnight at room temperature. After cooling, it is decomposed with 150 parts of a saturated ammonium chloride solution at a temperature of about 15° C. The whole is poured onto water and extracted with ether. The organic phase is washed four times with water, dried, filtered and upon acidification of the filtrate with 2-propanol, previously saturated with gaseous hydrogen chloride, an oil is separated. The ether is decanted and the oil is triturated twice in ether. The latter is decanted each time and the oily product is dissolved in water. Concentrated hydrochloric acid solution is added (150 parts) and the whole is stirred with activated charcoal. The latter is filtered off and the filtrate is boiled for 10 minutes and extracted with ether. The combined extracts are washed with water, dried, filtered and evaporated, yielding p-(1-hydroxyethyl)phenyl 2-thienyl ketone, as an oily residue.

To a stirred and cooled solution of 43.7 parts of p-(1-hydroxyethyl)phenyl 2-thienyl ketone in 180 parts of dry benzene are added dropwise 16 parts of thionyl chloride. Upon completion, stirring is continued overnight at room temperature. The reaction mixture is evaporated. The residue is taken up in toluene and the latter is evaporated once more. The latter residue is distilled and the distillate is crystallized from ethanol at room temperature, yielding p-(1-chloroethyl)phenyl 2-thienyl ketone; mp. 60° C.

A suspension of 4.9 parts of sodium cyanide in 55 parts of dimethyl sulfoxide is stirred while heating to 60° C. Then there are added at once 8.5 parts of p-(1-chloroethyl)phenyl 2-thienyl ketone and stirring at 60° C is continued for 4h.30. The reaction mixture is poured onto water and the product is extracted with ether. The organic layer is washed with water, dried, filtered and evaporated, yielding p-(2-thenoyl)hydratroponitrile as a residue.

EXAMPLE XXX

A mixture of 14.7 parts of 2'-methyl-3'-(2-thenoyl)acetophenone and 40 parts of methanol is stirred, while cooling on an ice-bath. Then there are added at once 0.6 parts of sodium borohydride. The reaction mixture is stirred overnight at room temperature and 50 parts of water are added. The methanol is evaporated and the product is extracted with ether. The extract is washed twice with water, dried, and evaporated in vacuo, yielding 3-(1-hydroxyethyl)-o-tolyl 2-thienyl ketone as a residue.

A mixture of 14.7 parts of 3-(1-hydroxyethyl)-o-tolyl 2-thienyl ketone and 126 parts of benzene is stirred while cooling on an ice-bath. Then 9.5 parts of thionyl chloride are added and the whole is stirred further over week-end at room temperature. The reaction mixture is evaporated in vacuo, yielding 3-(1-chloroethyl)-o-tolyl 2-thienyl ketone as a residue.

To a stirred and hot (60° C) solution of 7.35 parts of sodium cyanide and 30 parts of dimethyl sulfoxide is added a solution of 14.5 parts of 3-(1-chloroethyl)-o-tolyl 2-thienyl ketone in 30 parts of dimethyl sulfoxide.

The whole is stirred for 2h.30 at 60° C. The reaction mixture is cooled and poured onto water. The oily product is extracted twice with ether. The extract is dried and evaporated. The product is further purified twice by column-chromatography over silicagel, using chloroform as eluent, yielding in a second fraction, 2-methyl-3-(2-thenoyl)hydratroponitrile as a residue.

A mixture of 6 parts of 2-methyl-3-(2-thenoyl)hydratroponitrile, 2.7 parts of potassium hydroxide, 28 parts of ethanol and 3.5 parts of water is stirred and refluxed for 44 hours. The reaction mixture is evaporated. The residue is taken up in water and washed twice with 80 parts of ether. The aqueous phase is acidified with concentrated hydrochloric acid solution. The separated oily product is extracted with ether. Then the latter is dried and evaporated. The oily residue solidifies on triturating in petroleumether. The product is crystallized from acetonitrile at −20° C, yielding a first fraction of 2-methyl-3-(2-thenoyl)hydratropic acid; mp. 118.7° C. The mother-liquor is evaporated. The residue solidifies on triturating in petroleumether, yielding a second fraction of 2-methyl-3-(2-thenoyl)hydratropic acid; mp. 100° C.

EXAMPLE XXXI 11.4 parts of 2-[p-(2-thenoyl)phenyl]acetonitrile, 4.9 parts of methyl bromide and 0.13 parts of benzyl triethyl ammonium chloride are added to 30 parts of a 50% sodium hydroxide solution. The whole is stirred vigorously for 5 hours at 35° C. Distilled water is added. The organic layer is separated, washed with distilled water and evaporated. The oily residue is distilled, yielding p-(2-thenoyl)hydratroponitrile.

EXAMPLE XXXII

To a stirred and cooled (0° C) mixture of 4.2 parts of thiophene, 13 parts of stannic chloride and 40 parts of methylene chloride is added dropwise a solution of 10.2 parts of p-(1-chloroethyl)benzoyl chloride in 20 parts of methylene chloride (exothermic reaction with gaseous hydrogen chloride evolution). After stirring for 2h.30 the reaction mixture is poured onto a mixture of crushed ice and hydrochloric acid solution. The product is extracted with methylene chloride. The organic layer is separated, washed with alkaline water, dried and evaporated. The solid residue is triturated with hot petroleumether. The product is filtered off and crystallized from ethanol, yielding p-(1-chloroethyl)phenyl 2-thienyl ketone.

EXAMPLE XXXIII

A mixture of 1 part of sodium hydroxide in 96 parts of 2-propanol is heated to reflux and stirred till a homogenous mixture is obtained. Then there are added 6.25 parts of p-(2-thenoyl)hydratropic acid and the whole is stirred at reflux for one hour. The mixture is treated with 0.5 parts of activated charcoal and filtered over diatomaceous earth. After stirring the filtrate for 24 hours at room temperature, the product is filtered off and dried in vacuo over calcium chloride at 70° C, yielding p-(2-thenoyl)hydratropic acid, sodium salt; mp. 187.4° C.

To a stirred mixture of 28.2 parts of p-(2-thenoyl)hydratropic acid, sodium salt and 250 parts of hexamethylphosphoramide are added 56.8 parts of methyl iodide at room temperature (slightly exothermic reaction). The whole is stirred at room temperature for 1 hour. The reaction mixture is poured onto 1000 parts of water and the product is extracted three times with 140 parts of diisopropylether. The combined extracts are washed with 200 parts of water, dried, filtered and evaporated. The residue is crystallized from 35 parts of diisopropylether at 0° C, washed with cooled ether and dried, yielding methyl p-(2-thenoyl)hydratropate; mp. 62° C.

EXAMPLE XXXIV

To a stirred solution of 28.2 parts of p-(2-thenoyl)hydratropic acid, sodium salt in 250 parts of hexamethylphosphoramide are added 49.2 parts of 1-bromopropane and the whole is stirred for 2 hours at room temperature. The reaction mixture is poured onto 1000 parts of water and the product is extracted three times with diisopropylether. The combined extracts are washed with 200 parts of water, dried, filtered and evaporated. The viscous residue is filtered off over hyflo, yielding propyl p-(2-thenoyl)hydratropate as a yellow oil.

EXAMPLE XXXV

A mixture of 4.27 parts of lithium diisopropylamide and 50 parts of tetrahydrofuran is cooled to −78° C. Then there are added 10.4 parts of methyl 2-[p-(2-thenoyl)phenyl]acetate and the mixture is stirred for 40 minutes. 6.25 Parts of methyl iodide dissolved in 2.15 parts of hexamethylphosphoramide are added at −78° C and the mixture is further stirred for one hour after which it is allowed to warm up to room temperature. The whole is poured onto water. The resulting mixture is extracted with diisopropylether. The organic phase is washed with water, dried and evaporated. The residue is crystallized from diisopropylether at 0° C, yielding methyl p-(2-thenoyl)hydratropate.

EXAMPLE XXXVI

Gaseous ammonia is introduced through a solution of 5.8 parts of p-(2-thenoyl)hydratropoyl chloride in 80 parts of ether; the product is precipitated as an oil. The solvent is decanted and the oil is stirred in petroleumether. The solvent is decanted each time. The oily residue is dissolved in 2-propanol and the solvent is evaporated. The residue is dissolved in ether and upon the addition of petroleumether, the product is precipitated. It is filtered off and purified by column-chromatography over silicagel, using a mixture of chloroform, methanol and acetone (8 : 1 : 1 by volume). The pure fractions are collected and the solvent is evaporated. The oily residue is triturated in ether. The solid product is filtered off and dried, yielding p-(2-thenoyl)hydratropamide; mp. 108°–124° C.

EXAMPLE XXXVII

To a stirred mixture of 2.78 parts of p-(2-thenoyl)hydratropoyl chloride in 30 parts of dioxane are added 1.86 parts of aniline (exothermic reaction: temperature rises to 40° C). Upon completion, stirring is continued for 3 hours at reflux temperature. The reaction mixture is cooled to room temperature, filtered and the filtrate is boiled with activated charcoal. The latter is filtered off and the filtrate is evaporated. The residue is boiled in ether. The solvent is decanted and evaporated. The latter residue is purified by thin-layer-chromatography, using chloroform as eluent. The resulting oily product solidifies on scratching in ether. The solid product is filtered off and crystallized from 2-propanol at −20° C, yeilding p-(2-thenoyl)hydratropanilide; mp. 139.8° C.

EXAMPLE XXXVIII

To a stirred solution of 3.8 parts of p-chloroaniline in 20 parts of dioxane is added a solution of 4.2 parts of p-(2-thenoyl)hydratropoyl chloride in 25 parts of dioxane. The whole is diluted with 50 parts of dioxane and stirred and refluxed for 3 hours. The reaction mixture is cooled to room temperature, filtered and the filtrate is evaporated. The residue is boiled twice with ether to remove the last traces p-chloroaniline and filtered each time. The solid product is crystallized from 2-propanol at −20° C, yielding, after drying in vacuo, 4'-chloro-4-(2-thenoyl)hydratropanilide; mp. 169.4° C.

EXAMPLE XXXIX

To a stirred solution of 3.2 parts of p-toluidine in 20 parts of dioxane is added a solution of 4.2 parts of p-(2-thenoyl)hydratropoyl chloride in 25 parts of dioxane and the whole is stirred and refluxed for 3 hours. The reaction mixture is allowed to cool to room temperature and filtered. The filtrate is treated with activated charcoal, filtered and the filtrate is evaporated. The solid residue is stirred in ether, filtered off and crystallized from 2-propanol, yielding, after drying in vacuo, p-(2-thenoyl)hydratropo-p-toluidide; mp. 158.3° C.

EXAMPLE XL

To a stirred solution of 2.55 parts of piperidine in 20 parts of dioxane is added a solution of 4.2 parts of p-(2-thenoyl)hydratropoyl chloride in 25 parts of dioxane. The whole is stirred and refluxed for 30 minutes. The reaction mixture is allowed to cool to room temperature, filtered and evaporated in vacuo. The oily residue is purified by column-chromatography over silicagel, using chloroform as eluent. The pure oily fractions are collected and solidfied on scratching in petroleumether. The solid product is filtered off, yielding, after drying in vacuo, 1-[p-(2-thenoyl)hydratropoyl]piperidine; mp. 70.3° C.

EXAMPLE XLI

To a stirred solution of 2.44 parts of 2-aminoethanol in 15 parts of chloroform is added dropwise a solution of 5.6 parts of p-(2-thenoyl)hydratropoyl chloride in 15 parts of chloroform at room temperature (highly exothermic reaction). Upon completion, the whole is stirred and refluxed for one hour. The reaction mixture is cooled and washed with a 1N hydrochloric acid solution. The organic layer is separated, washed twice with water, dried, filtered and evaporated. The oily residue solidifies on triturating in petroleumether. The solid product is filtered off and crystallized from boiling ether, yielding N-(2-hydroxyethyl)-p-(2-thenoyl)hydratropamide; mp. 87.1° C.

EXAMPLE XLII

To a stirred and cooled mixture of 28.4 parts of 2-chloro-m-toluoyl chloride, 12.6 parts of thiophene and 80 parts of methylene chloride is added dropwise a mixture of 39 parts of stannic chloride in 40 parts of methylene chloride at 10° C. Upon completion, stirring is continued first for 2 hours at 20° C and further for 3 hours at reflux. The reaction mixture is poured onto a mixture of ice-water and concentrated hydrochloric acid solution. The methylene chloride solution is separated, washed three times with water, dried, filtered and evaporated. The residue is distilled, yielding 2-chlorom-tolyl 2-thienyl ketone; bp. 197°-199° C at 12 mm. pressure.

A mixture of 11.8 parts of 2-chloro-m-tolyl 2-thienyl ketone, 8.9 parts of N-bromosuccinimide, 100 parts of carbon tetrachloride and 0.25 parts of benzoyl peroxide is stirred and refluxed for 2 hours. The precipitated succinimide if filtered off and washed on the filter which carbon tetrachloride. The filtrate is dried and evaporated, yielding α-bromo-2-chloro-m-tolyl 2-thienyl ketone as a residue.

To a stirred and hot solution of 7.35 parts of sodium cyanide in 50 parts of dimethyl sulfoxide is added dropwise a solution of 15.2 parts of α-bromo-2-chloro-m-tolyl 2-thienyl ketone in 25 parts of dimethyl sulfoxide at 60° C. Upon completion, stirring is continued for 2 hours at 60° C. The reaction mixture is poured onto water and the product is extracted three times with 240 parts of ether. The combined ether phases are washed three times with 100 parts of water, dried, filtered and evaporated. The residue is boiled four times in 80 parts of diisopropylether and the latter is each time decanted, yielding 2-[2-chloro-3-(2-thenoyl)phenyl]acetonitrile as a residue which solidifies on standing.

A mixture of 4.2 parts of 2-[2-chloro-3-(2-thenoyl)-phenyl]acetonitrile, 7 parts of acetic acid, 7 parts of water and 12 parts of sulfuric acid is stirred and boiled for 1h.30. The reaction mixture is cooled, poured onto water and extracted with ether. The extract is washed with water, extracted with 50 parts of a 5% sodium hydroxide solution and the alkaline solution is washed with ether. After acidification with diluted hydrochloric acid solution, the whole is extracted again with ether. The extract is washed with water, treated with charcoal, filtered and evaporated. The residue is purified by column-chromatography over silicagel, using a mixture of chloroform and 5% of methanol as eluent. The pure fractions are collected and the eluent is evaporated, yielding 2-[2-chloro-3-(2-thenoyl)phenyl]acetic acid; mp. 112.2° C.

EXAMPLE XLIII

To a stirred mixture of 26 parts of 2-[p-(2-thenoyl)-phenyl]acetonitrile, 34 parts of 1,2-dibromoethane and 1.6 parts of benzyl triethyl ammonium chloride are added dropwise 60 parts of sodium hydroxide solution 20N (exothermic reaction:temperature rises to 50° C — cooling is necessary to keep the temperature at 50° C). Upon completion, stirring at 50° C is continued for 4 hours. The product is extracted with toluene. The organic layer is separated, washed three times with water, dried, filtered and evaporated. The solid residue is crystallized from acetonitrile, yielding 12.2 parts of 1-[p-(2-thenoyl)phenyl]cyclopropanecarbonitrile; mp. 105.8° C.

A mixture of 10 parts of 1-[p-(2-thenoyl)phenyl]cyclopropanecarbonitrile, 3.92 parts of potassium hydroxide, 35 parts of ethylene glycol and 3.5 parts of water is stirred for 48 hours while heating at 140° C. The reaction mixture is poured onto water, stirred with activated charcoal and filtered over hyflo. The filtrate is acidified with hydrochloric acid and the product is extracted with ether. The latter is washed with water, dried, filtered and evaporated. The solid residue is crystallized from acetonitrile, yielding 6.1 parts of 1-[p-(2thenoyl)-phenyl]cyclopropanecarboxylic acid; mp. 165.9° C (dec.).

EXAMPLE XLIV

A mixture of 4.2 parts of 1-[p-(2-thenoyl)phenyl]cyclopropanecarbonyl chloride and 50 parts of ammonium hydroxide is stirred for 3 hours. The precipitated product is filtered off, washed with water, dried and crystallized from 2-propanol, yielding 2 parts of 1-[p-(2-thenoyl)phenyl]cyclopropanecarboxamide; mp. 173.7° C (dec.).

EXAMPLE XLV

Following the procedure of Example XLIII and using therein equivalent amount respectively of an appropriate aroylphenylacetonitrile and of an appropriate dibromoalkane, the following compounds are prepared:
1-[4-(2-thenoyl)phenyl]cyclobutanecarboxylic acid;
1-[4-(2-thenoyl)phenyl]cyclopentanecarboxylic acid;
1-[4-(2-thenoyl)phenyl]cyclohexanecarboxylic acid;
1-[2-chloro-3-(2-thenoyl)phenyl]cyclopropanecarboxylic acid;
1-[2-chloro-3-(2-thenoyl)phenyl]cyclobutanecarboxylic acid;
1-[2-chloro-3-(2-thenoyl)phenyl]cyclopentanecarboxylic acid; and
1-[2-chloro-3-(2-thenoyl)phenyl]cyclohexanecarboxylic acid.

EXAMPLE XLVI

Following the procedure of Example XXI and using therein equivalent amounts respectively of an appropriate aroylphenylacetic acid and of an appropriately substituted amine, the following compounds are prepared:
3-chloro-4-(2-thenoyl)hydratropanilide;
4-(3-pyridinylcarbonyl)hydratropanilide;
4-(5-methyl-2-thenoyl)hydratropanilide;
4-(2-naphthoyl)hydratropailide;
3-(2-thenoyl)hydratropanilide;
2-[4-(2-thenoyl)phenyl]-4-pentenoanilide;
4'-chloro-1-[4(2-thenoyl)phenyl]cyclopropanecarboxanilide;
4'-chloro-2-[4-(2-thenoyl)phenyl]hexanoanilide;
3-chloro-4-(2-thenoyl)hydratropo-4-anisidide;
4-(3-pyridylcarbonyl)hydratropo-4-anisidide;
3-chloro-N-(2-hydroxyethyl)-4-(2-thenoyl)hydratropamide;
3-chloro-4-(2-thenoyl)hydratropo-4-toluidide;
1-[3-chloro-4-(2-thenoyl)hydratropoyl]piperidine;
3-chloro-N-(2-thiazolin-2-yl)-4-(2-thenoyl)hydratropamide; and
N-(2-thiazolin-2-yl)-1-[4-(2-thenoyl)phenyl]cyclopropanecarboxamide.

EXAMPLE XLVII

Following the procedure of Example XXIII and using an equivalent amount of an appropriately substituted alkyl aroylphenylacetate in place of the ethyl 4-(2-thenoyl)hydratropate used therein, the following compounds are prepared:
4-(3-pyridylcarbonyl)hydratropohydroxamic acid;
2-[4-(2-thenoyl)phenyl]butyrohydroxamic acid;
2-[4-(2-thenoyl)phenyl]-4pentenohydroxamic acid;
3-(2-thenoyl)hydratropohydroxamic acid;
4-(2-naphthoyl)hydratropohydroxamic acid;
4-(5-methyl-2-thenoyl)hydratropohydroxamic acid; and
3-chloro-4-(2-thenoyl)hydratropohydroxamic acid.

What is claimed is:
1. A diloweralkyl malonate having the formula:

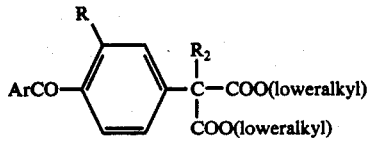

wherein:

ArCO is an aroyl substituent the Ar function of which is a member selected from the group consisting of 2-thienyl, 5-methyl-2-thienyl, 5-chloro-2-thienyl, 2-naphthyl and 3-pyridyl;

R is a member selected from the group consisting of hydrogen, loweralkyl and halo, provided that when said R is halo, then said Ar is 2-thienyl-5-methyl-2-thienyl or 5-chloro2-thienyl;

$R_2$ is a member selected from the group consisting of hydrogen, allyl and loweralkyl.

2. Diethyl 2-methyl-2-[p-(2-thenoyl)phenyl]malonate.

3. Diethyl 2-[3-chloro-4-(2-thenoyl)phenyl]-2-methylmalonate.

4. Diethyl 2-methyl-2-[p-(3-pyridylcarbonyl)phenyl]-malonate.

5. Diethyl 2-methyl-2-[p-(5-methyl-2-thenoyl)-phenyl]-malonate.

6. Diethyl 2-methyl-2-[p-(2-naphthoyl)phenyl]malonate.

7. Diethyl 2-ethyl-2-[p-(2thenoyl)phenyl]malonate.

8. Diethyl 2-allyl-2-[p-(2-thenoyl)phenyl]malonate.

9. Diethyl 2-methyl-2-[p-(2-thenoyl)-m-tolyl]malonate.

* * * * *

UNITED STATES PATENT AND TRADEMARK OFFICE
CERTIFICATE OF CORRECTION

PATENT NO. : 4,060,528

DATED : November 29, 1977

INVENTOR(S) : Paul Adriaan Jan Janssen; Georges Henri Paul Van Daele; Jozef Martin Boey It is certified that error appears in the above-identified patent and that said Letters Patent are hereby corrected as shown below:

At Column 5, Line 32, "n" should be -- in --.
At Column 10, Line 46, "is" should be deleted.
At Column 14, Line 51, "an" should be -- a --.
At Column 19, Line 65, "shown" should be -- show --.
At Column 28, Line 27, "4parts" should be -- 4 parts --.
At Column 37, Line 41, after "is stirred" insert -- twice --.

Signed and Sealed this

Twelfth Day of December 1978

[SEAL]

Attest:

RUTH C. MASON
Attesting Officer

DONALD W. BANNER
Commissioner of Patents and Trademarks